United States Patent
Maschino et al.

(10) Patent No.: US 7,801,601 B2
(45) Date of Patent: Sep. 21, 2010

(54) CONTROLLING NEUROMODULATION USING STIMULUS MODALITIES

(75) Inventors: Steven E. Maschino, Seabrook, TX (US); David Thompson, Houston, TX (US)

(73) Assignee: Cyberonics, Inc., Houston, TX (US)

( * ) Notice: Subject to any disclaimer, the term of this patent is extended or adjusted under 35 U.S.C. 154(b) by 1067 days.

(21) Appl. No.: 11/341,956

(22) Filed: Jan. 27, 2006

(65) Prior Publication Data

US 2007/0179557 A1 Aug. 2, 2007

(51) Int. Cl.
*A61N 1/18* (2006.01)
(52) U.S. Cl. .................................... 607/2; 607/46
(58) Field of Classification Search .................. 607/45, 607/2, 46
See application file for complete search history.

(56) References Cited

U.S. PATENT DOCUMENTS

| | | | |
|---|---|---|---|
| 3,796,221 A | 3/1974 | Hagfors |
| 4,305,402 A | 12/1981 | Katims |
| 4,431,000 A | 2/1984 | Butler et al. |
| 4,503,863 A | 3/1985 | Katims |
| 4,556,064 A | 12/1985 | Pomeranz et al. |
| 4,573,481 A | 3/1986 | Bullara |
| 4,702,254 A | 10/1987 | Zabara |
| 4,745,923 A | 5/1988 | Winstrom |
| 4,867,164 A | 9/1989 | Zabara |
| 4,873,655 A | 10/1989 | Kondraske |
| 4,949,721 A | 8/1990 | Toriu et al. |
| 4,958,632 A | 9/1990 | Duggan |
| 5,025,807 A | 6/1991 | Zabara |
| 5,081,987 A | 1/1992 | Nigam |
| 5,084,007 A | 1/1992 | Malin et al. |
| 5,111,815 A | 5/1992 | Mower |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,201,808 A | 4/1993 | Steinhaus et al. |
| 5,203,326 A | 4/1993 | Collins |

(Continued)

FOREIGN PATENT DOCUMENTS

EP 1070518 A2 1/2001

(Continued)

OTHER PUBLICATIONS

PCT/US2007/000344 Search Report (Aug. 21, 2007).

(Continued)

*Primary Examiner*—Carl H Layno
*Assistant Examiner*—Brian T Gedeon
(74) *Attorney, Agent, or Firm*—Williams, Morgan & Amerson, P.C.; Timothy L. Scott

(57) ABSTRACT

A method, apparatus, and system for affecting neuromodulation based upon an evoking signal applied to a patient's body. An internal and/or external evoking and/or therapeutic signal is applied to a first target portion of a patient's body. Data relating to a physiological response resulting from the internal and/or external evoking and/or therapeutic signal is received. A neurotransmission characteristic of the patient's body is determined based upon the data relating to the physiological response. At least one parameter defining an electrical therapeutic signal provided by an implantable medical device is controlled based upon the determined neurotransmission characteristic to treat a disorder.

15 Claims, 15 Drawing Sheets

U.S. PATENT DOCUMENTS

| | | |
|---|---|---|
| 5,205,285 A | 4/1993 | Baker, Jr. |
| 5,215,086 A | 6/1993 | Terry, Jr. et al. |
| 5,222,494 A | 6/1993 | Baker, Jr. |
| 5,231,988 A | 8/1993 | Wernicke et al. |
| 5,263,480 A | 11/1993 | Wernicke et al. |
| 5,269,302 A | 12/1993 | Swartz et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,311,876 A | 5/1994 | Olsen et al. |
| 5,330,515 A | 7/1994 | Rutecki et al. |
| 5,335,657 A | 8/1994 | Terry, Jr. et al. |
| 5,366,435 A | 11/1994 | Jacobson |
| 5,441,495 A | 8/1995 | Liboff et al. |
| 5,458,625 A | 10/1995 | Kendall |
| 5,465,711 A | 11/1995 | Moll et al. |
| 5,501,702 A | 3/1996 | Plicchi et al. |
| 5,501,704 A | 3/1996 | Chang et al. |
| 5,522,862 A | 6/1996 | Testerman et al. |
| 5,540,730 A | 7/1996 | Terry, Jr. et al. |
| 5,540,734 A | 7/1996 | Zabara |
| 5,569,186 A | 10/1996 | Lord et al. |
| 5,601,435 A | 2/1997 | Quy |
| 5,611,350 A | 3/1997 | John |
| 5,644,234 A | 7/1997 | Rasche et al. |
| 5,645,570 A | 7/1997 | Corbucci |
| 5,658,318 A | 8/1997 | Stroetmann et al. |
| 5,683,422 A | 11/1997 | Rise |
| 5,690,688 A | 11/1997 | Noren et al. |
| 5,702,429 A | 12/1997 | King |
| 5,707,334 A | 1/1998 | Young |
| 5,707,400 A | 1/1998 | Terry, Jr. et al. |
| 5,716,377 A | 2/1998 | Rise et al. |
| 5,725,471 A | 3/1998 | Davey et al. |
| 5,738,625 A | 4/1998 | Gluck |
| 5,743,860 A | 4/1998 | Hively et al. |
| 5,769,778 A | 6/1998 | Abrams et al. |
| 5,792,186 A | 8/1998 | Rise |
| 5,800,474 A | 9/1998 | Benabid et al. |
| 5,814,092 A | 9/1998 | King |
| 5,833,600 A | 11/1998 | Young |
| 5,833,709 A | 11/1998 | Rise et al. |
| 5,861,014 A | 1/1999 | Familoni |
| 5,899,922 A | 5/1999 | Loos |
| 5,913,882 A | 6/1999 | King |
| 5,916,239 A | 6/1999 | Geddes et al. |
| 5,928,272 A | 7/1999 | Adkins et al. |
| 5,941,906 A | 8/1999 | Barreras, Sr. et al. |
| 5,978,702 A | 11/1999 | Ward et al. |
| 5,987,352 A | 11/1999 | Klein et al. |
| 5,995,868 A | 11/1999 | Dorfmeister et al. |
| 6,016,449 A | 1/2000 | Fischell et al. |
| 6,018,682 A | 1/2000 | Rise |
| 6,061,593 A | 5/2000 | Fischell et al. |
| 6,066,084 A | 5/2000 | Edrich et al. |
| 6,081,744 A | 6/2000 | Loos |
| 6,083,249 A | 7/2000 | Familoni |
| 6,104,956 A | 8/2000 | Naritoku et al. |
| 6,109,269 A | 8/2000 | Rise et al. |
| 6,128,538 A | 10/2000 | Fischell et al. |
| 6,129,685 A | 10/2000 | Howard, III |
| 6,132,361 A | 10/2000 | Epstein et al. |
| 6,134,474 A | 10/2000 | Fischell et al. |
| 6,141,590 A | 10/2000 | Renirie et al. |
| 6,161,044 A | 12/2000 | Silverstone |
| 6,167,311 A | 12/2000 | Rezai |
| 6,176,242 B1 | 1/2001 | Rise |
| 6,179,771 B1 | 1/2001 | Mueller |
| 6,198,958 B1 | 3/2001 | Ives et al. |
| 6,205,359 B1 | 3/2001 | Boveja |
| 6,208,894 B1 | 3/2001 | Schulman et al. |
| 6,208,902 B1 | 3/2001 | Boveja |
| 6,221,908 B1 | 4/2001 | Kilgard et al. |
| 6,234,953 B1 | 5/2001 | Thomas et al. |
| 6,248,080 B1 | 6/2001 | Miesel et al. |
| 6,253,109 B1 | 6/2001 | Gielen |
| 6,266,556 B1 | 7/2001 | Ives et al. |
| 6,280,376 B1 | 8/2001 | Holcomb |
| 6,304,775 B1 | 10/2001 | Iasemidis et al. |
| 6,319,241 B1 | 11/2001 | King et al. |
| 6,327,503 B1 | 12/2001 | Familoni |
| 6,337,997 B1 | 1/2002 | Rise |
| 6,339,725 B1 | 1/2002 | Naritoku et al. |
| 6,341,236 B1 | 1/2002 | Osorio et al. |
| 6,353,762 B1 | 3/2002 | Baudino et al. |
| 6,356,784 B1 | 3/2002 | Lozano et al. |
| 6,356,788 B2 | 3/2002 | Boveja |
| 6,360,122 B1 | 3/2002 | Fischell et al. |
| 6,366,813 B1 | 4/2002 | DiLorenzo |
| 6,366,814 B1 | 4/2002 | Boveja et al. |
| 6,381,496 B1 | 4/2002 | Meadows et al. |
| 6,397,100 B2 | 5/2002 | Stadler et al. |
| 6,405,732 B1 | 6/2002 | Edwards et al. |
| 6,418,344 B1 | 7/2002 | Rezai et al. |
| 6,425,852 B1 | 7/2002 | Epstein et al. |
| 6,427,086 B1 | 7/2002 | Fischell et al. |
| 6,449,507 B1 | 9/2002 | Hill et al. |
| 6,459,936 B2 | 10/2002 | Fischell et al. |
| 6,463,328 B1 | 10/2002 | John |
| 6,466,822 B1 | 10/2002 | Pless |
| 6,473,639 B1 | 10/2002 | Fischell et al. |
| 6,473,644 B1 | 10/2002 | Terry, Jr. et al. |
| 6,473,653 B1 | 10/2002 | Schallhorn et al. |
| 6,477,417 B1 | 11/2002 | Levine |
| 6,477,418 B2 | 11/2002 | Plicchi et al. |
| 6,480,743 B1 | 11/2002 | Kirkpatrick et al. |
| 6,491,620 B1 | 12/2002 | Davey |
| 6,500,110 B1 | 12/2002 | Davey et al. |
| 6,505,074 B2 | 1/2003 | Boveja et al. |
| 6,522,928 B2 | 2/2003 | Whitehurst et al. |
| 6,527,695 B1 | 3/2003 | Davey et al. |
| 6,529,774 B1 | 3/2003 | Greene |
| 6,532,388 B1 | 3/2003 | Hill et al. |
| 6,549,804 B1 | 4/2003 | Osorio et al. |
| 6,551,233 B2 | 4/2003 | Perreault et al. |
| 6,556,868 B2 | 4/2003 | Naritoku et al. |
| 6,560,486 B1 | 5/2003 | Osorio et al. |
| 6,561,968 B1 | 5/2003 | Dissing et al. |
| 6,564,102 B1 | 5/2003 | Boveja |
| 6,567,702 B1 | 5/2003 | Nekhendzy et al. |
| 6,571,123 B2 | 5/2003 | Ives et al. |
| 6,572,528 B2 | 6/2003 | Rohan et al. |
| 6,587,719 B1 | 7/2003 | Barrett et al. |
| 6,587,727 B2 | 7/2003 | Osorio et al. |
| 6,591,138 B1 | 7/2003 | Fischell et al. |
| 6,594,524 B2 | 7/2003 | Esteller et al. |
| 6,609,025 B2 | 8/2003 | Barrett et al. |
| 6,609,030 B1 | 8/2003 | Rezai et al. |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,625,492 B2 | 9/2003 | Florio et al. |
| 6,628,987 B1 | 9/2003 | Hill et al. |
| 6,647,296 B2 | 11/2003 | Fischell et al. |
| 6,668,191 B1 | 12/2003 | Boveja |
| 6,671,547 B2 | 12/2003 | Lyster et al. |
| 6,671,555 B2 | 12/2003 | Gielen et al. |
| 6,671,556 B2 | 12/2003 | Osorio et al. |
| 6,684,104 B2 | 1/2004 | Gordon et al. |
| 6,684,105 B2 | 1/2004 | Cohen et al. |
| 6,690,974 B2 | 2/2004 | Archer et al. |
| 6,708,064 B2 | 3/2004 | Rezai |

| | | | |
|---|---|---|---|
| 6,721,603 B2 | 4/2004 | Zabara et al. | |
| 6,735,475 B1 | 5/2004 | Whitehurst et al. | |
| 6,760,626 B1 | 7/2004 | Boveja | |
| 6,768,969 B1 | 7/2004 | Nikitin et al. | |
| 6,785,568 B2 | 8/2004 | Chance | |
| 6,788,975 B1 | 9/2004 | Whitehurst et al. | |
| 6,793,670 B2 | 9/2004 | Osorio et al. | |
| 6,801,805 B2 | 10/2004 | Stokes et al. | |
| 6,819,210 B2 | 11/2004 | Boynton et al. | |
| 6,819,953 B2 | 11/2004 | Yonce et al. | |
| 6,819,956 B2 | 11/2004 | DiLorenzo | |
| 6,819,958 B2 | 11/2004 | Weiner et al. | |
| 6,827,681 B2 | 12/2004 | Tanner et al. | |
| 6,830,544 B2 | 12/2004 | Tanner | |
| 6,832,114 B1 | 12/2004 | Whitehurst et al. | |
| 6,836,685 B1 | 12/2004 | Fitz | |
| 6,848,448 B1 | 2/2005 | St. Germain et al. | |
| 6,849,040 B2 | 2/2005 | Ruohonen et al. | |
| 6,853,862 B1 | 2/2005 | Marchal et al. | |
| 6,885,888 B2 | 4/2005 | Rezai | |
| 6,889,076 B2 | 5/2005 | Cigaina | |
| 6,904,390 B2 | 6/2005 | Nikitin et al. | |
| 6,920,357 B2 | 7/2005 | Osorio et al. | |
| 6,934,580 B1 | 8/2005 | Osorio et al. | |
| 6,944,501 B1 | 9/2005 | Pless | |
| 6,961,618 B2 | 11/2005 | Osorio et al. | |
| 7,006,859 B1 | 2/2006 | Osorio et al. | |
| 7,006,872 B2 | 2/2006 | Gielen et al. | |
| 7,010,351 B2 | 3/2006 | Firlik et al. | |
| 7,050,856 B2 | 5/2006 | Stypulkowski | |
| 7,054,686 B2 | 5/2006 | MacDonald | |
| 7,054,792 B2 | 5/2006 | Frei et al. | |
| 7,076,288 B2 | 7/2006 | Skinner | |
| 7,146,218 B2 | 12/2006 | Esteller et al. | |
| 7,177,678 B1 | 2/2007 | Osorio et al. | |
| 7,188,053 B2 | 3/2007 | Nikitin et al. | |
| 7,204,833 B1 | 4/2007 | Osorio et al. | |
| 7,206,632 B2 * | 4/2007 | King | 600/544 |
| 7,206,640 B1 * | 4/2007 | Overstreet | 607/57 |
| 2002/0099412 A1 | 7/2002 | Fischell et al. | |
| 2002/0143368 A1 | 10/2002 | Bakels et al. | |
| 2002/0151939 A1 | 10/2002 | Rezai | |
| 2002/0169485 A1 | 11/2002 | Pless et al. | 607/48 |
| 2003/0083716 A1 | 5/2003 | Nicolelis et al. | |
| 2003/0097161 A1 | 5/2003 | Firlik et al. | |
| 2003/0181954 A1 | 9/2003 | Rezai | |
| 2003/0212440 A1 | 11/2003 | Boveja | |
| 2003/0236558 A1 | 12/2003 | Whitehurst et al. | |
| 2004/0133119 A1 | 7/2004 | Osorio et al. | |
| 2004/0138517 A1 | 7/2004 | Osorio et al. | |
| 2004/0153129 A1 | 8/2004 | Pless et al. | |
| 2004/0158165 A1 | 8/2004 | Yonce et al. | |
| 2004/0167583 A1 | 8/2004 | Knudson et al. | |
| 2004/0172085 A1 | 9/2004 | Knudson et al. | |
| 2004/0172089 A1 | 9/2004 | Whitehurst et al. | |
| 2004/0172091 A1 | 9/2004 | Rezai | |
| 2004/0172094 A1 | 9/2004 | Cohen et al. | |
| 2004/0176812 A1 | 9/2004 | Knudson et al. | |
| 2004/0193231 A1 | 9/2004 | David et al. | |
| 2004/0210270 A1 | 10/2004 | Erickson | |
| 2004/0210274 A1 | 10/2004 | Bauhahn et al. | |
| 2004/0249416 A1 | 12/2004 | Yun et al. | |
| 2004/0263172 A1 | 12/2004 | Gray et al. | |
| 2004/0267330 A1 | 12/2004 | Lee et al. | 607/48 |
| 2005/0004621 A1 | 1/2005 | Boveja et al. | |
| 2005/0021092 A1 | 1/2005 | Yun et al. | |
| 2005/0021103 A1 | 1/2005 | DiLorenzo | |
| 2005/0021104 A1 | 1/2005 | DiLorenzo | |
| 2005/0021105 A1 | 1/2005 | Firlik et al. | |
| 2005/0033379 A1 | 2/2005 | Lozano et al. | |
| 2005/0038484 A1 | 2/2005 | Knudson et al. | |
| 2005/0049655 A1 | 3/2005 | Boveja et al. | |
| 2005/0060010 A1 | 3/2005 | Goetz | |
| 2005/0065562 A1 | 3/2005 | Rezai | |
| 2005/0065573 A1 | 3/2005 | Rezai | |
| 2005/0065574 A1 | 3/2005 | Rezai | |
| 2005/0065575 A1 | 3/2005 | Dobak | |
| 2005/0070971 A1 | 3/2005 | Fowler et al. | |
| 2005/0075680 A1 | 4/2005 | Lowry et al. | 607/45 |
| 2005/0075681 A1 | 4/2005 | Rezai et al. | |
| 2005/0119703 A1 | 6/2005 | DiLorenzo | |
| 2005/0131485 A1 | 6/2005 | Knudson et al. | |
| 2005/0131506 A1 | 6/2005 | Rezai et al. | |
| 2005/0143786 A1 | 6/2005 | Boveja | |
| 2005/0153885 A1 | 7/2005 | Yun et al. | |
| 2005/0154425 A1 | 7/2005 | Boveja et al. | |
| 2005/0165458 A1 | 7/2005 | Boveja et al. | |
| 2005/0177200 A1 | 8/2005 | George et al. | |
| 2005/0187590 A1 | 8/2005 | Boveja et al. | |
| 2005/0277998 A1 | 12/2005 | Tracey et al. | |
| 2005/0283200 A1 | 12/2005 | Rezai et al. | |
| 2005/0283201 A1 | 12/2005 | Machado et al. | |
| 2005/0288760 A1 | 12/2005 | Machado et al. | |
| 2006/0009815 A1 | 1/2006 | Boveja et al. | |
| 2006/0015153 A1 * | 1/2006 | Gliner et al. | 607/45 |
| 2006/0074450 A1 | 4/2006 | Boveja et al. | |
| 2006/0079936 A1 | 4/2006 | Boveja et al. | |
| 2006/0095081 A1 | 5/2006 | Zhou et al. | |
| 2006/0111644 A1 | 5/2006 | Guttag et al. | |
| 2006/0129204 A1 | 6/2006 | Pless et al. | 607/45 |
| 2006/0200206 A1 | 9/2006 | Firlik et al. | |
| 2006/0212091 A1 | 9/2006 | Lozano et al. | |
| 2006/0224191 A1 | 10/2006 | Dilorenzo | |
| 2006/0259095 A1 | 11/2006 | Wyler et al. | |
| 2006/0293720 A1 | 12/2006 | DiLorenzo | |
| 2007/0032834 A1 | 2/2007 | Gliner et al. | |
| 2007/0055320 A1 | 3/2007 | Weinand | |
| 2007/0073355 A1 | 3/2007 | Dilorenzo | |
| 2007/0088403 A1 | 4/2007 | Wyler et al. | |
| 2007/0088404 A1 | 4/2007 | Wyler et al. | |
| 2007/0100392 A1 | 5/2007 | Maschino et al. | 607/45 |
| 2007/0142862 A1 | 6/2007 | Dilorenzo | |
| 2007/0142873 A1 | 6/2007 | Esteller et al. | |
| 2007/0150024 A1 | 6/2007 | Leyde et al. | |
| 2007/0161919 A1 | 7/2007 | DiLorenzo | |
| 2007/0162086 A1 | 7/2007 | DiLorenzo | |
| 2007/0167991 A1 | 7/2007 | DiLorenzo | |
| 2007/0179534 A1 | 8/2007 | Firlik et al. | |
| 2007/0179558 A1 | 8/2007 | Gliner et al. | |
| 2007/0179584 A1 | 8/2007 | Gliner | |
| 2007/0208212 A1 | 9/2007 | DiLorenzo | |
| 2007/0250145 A1 | 10/2007 | Kraus et al. | |
| 2008/0021520 A1 | 1/2008 | Dietrich | |
| 2008/0051852 A1 | 2/2008 | Dietrich et al. | |

FOREIGN PATENT DOCUMENTS

| | | |
|---|---|---|
| EP | 1145736 A2 | 10/2001 |
| WO | WO02/47760 | 6/2002 |
| WO | WO 03085546 A1 | 10/2003 |
| WO | WO 2004000413 A2 | 12/2003 |
| WO | WO 2005028026 A1 | 3/2004 |
| WO | WO 2004036377 A2 | 4/2004 |
| WO | WO 2004112894 A1 | 12/2004 |
| WO | WO 2005065768 A1 | 7/2005 |
| WO | WO 2005067599 A2 | 7/2005 |

OTHER PUBLICATIONS

Kähkönen et al., *NeuroImage* 24:955-960 (2005).
Bachman, D., S. et al.; "Effects Of Vagal Volleys And Serotonin On Units Of Cingulate Cortex in Monkeys," Brain Research, vol. 130 (1977). pp. 253-269.
Bohning, D.E., et al.; "Feasibility of Vagus Nerve Stimulation - Synchronized Blood Oxygenation Level-Dependent Functional MRI," A Journal of Clinical and Laboratory Research: Investigative Radiology; vol. 36, No. 8 (Aug. 2001); pp. 470-479.

Borovikova, L.V., et al.; "Vagus Nerve Stimulation Attenuates the Systemic Inflammatory Response to Endotoxin;" Letters to Nature; vol. 405; (May 2000); pp. 458-462.

Das, Atin; "Brain and Chaos: When Two Giants Meet;" http://www.cerebromente.org.br/n14/mente/chaos.html; 6 pgs.

Devous, Michael D., et al.; "Effects of Vagus Nerve Stimulation on Regional Cerebral Blood Flow in Treatment-Resistant Depression," National Institute of Mental Health - 42nd Annual NCDEU Meeting: Poster Session II; Poster Abstracts, Jun. 10-13, 2002, 1 page; http://www.nimh.nih.gov/ncdeu/abstracts2002/ncdeu2019.cfm.

Dietrich, S., et al., "A Novel Transcutaneous Vagus Nerve Stimulation Leads to Brainstem and Cerebral Activations Measured by Functional MRI;" Biomed Tech 2008, vol. 53, pp. 104-111.

Henry, T. R., et al.; "Brain Blood-Flow Alterations Induced by Therapeutic Vagus Nerve Stimulation inPartial Epilepsy: I. Acute Effects at High and Low Levels of Stimulation;" Epilepsia vol. 39, No. 9; pp. 984-990 (1998).

Kahkonen, S., et al.; Prefrontal Transcranial Magnetic Stimulaiton Produces Intensity-Dependent EEG Responses in Humans; NeuroImage, vol. 24, (2005) pp. 955-960.

King, M.D., "Effects of Short-Term Vagus Nerve Stimulation (VNS) on FOS Expression in Rat Brain Nuclei" 58th Annual Scientific Convention of the Society of Biological Psychiatry, (May, 2003)

Koo, B., "EEG Changes With Vagus Nerve Stimulation" Journal of Clinical Neurophysiology, vol. 18, No. 5 (Sep. 2001); pp. 434-441.

Rogers, R.C. et al.; "Central Regulation of Brainstem Gastric Vago-Vagal Control Circuits" Neuroanatomy and Phsiology of Abdominal Vagal Afferents, Ch. 5 (1992); pp. 100-134.

Sheikh, S., M.D., et al.; "Effects of Vagus Nerve Stimulation Therapy on Brain Metabolism in Severe, Chronic Treatment-Resistant Depression:One-Year Outcome" 58th Annual Scientific Convention of the Society of Biological Psychiatry (May 2003).

Terry et al.; "The Implantable Neurocybemetic Prosthesis System", Pacing and Clinical Electrophysiology, vol. 14, No. 1 (Jan. 1991), pp. 86-93.

Zabara, J. "Inhibition of Experimental Seizures in Canines by Repetivie Vagal Stimulation" Epilepsis vol. 33, No. 6 (1992); pp. 1005-1012.

* cited by examiner

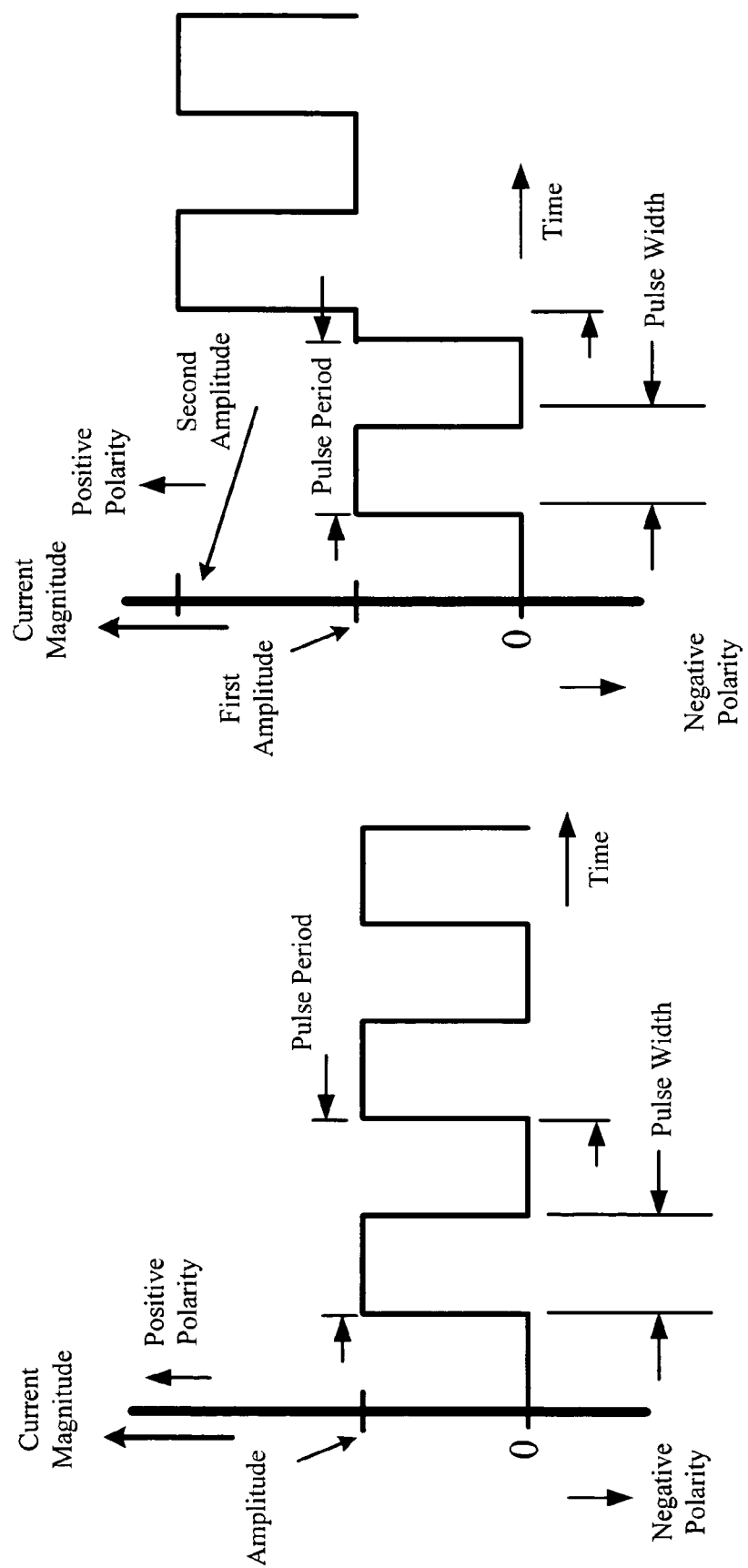

CONTROLLING NEUROMODULATION USING STIMULUS MODALITIES

BACKGROUND OF THE INVENTION

1. Field of the Invention

This invention relates generally to implantable medical devices and, more particularly, to methods, apparatus, and systems for affecting neuromodulation using an external evoking signal and/or an internal evoking signal to control a therapeutic stimulation signal applied by a medical device.

2. Description of the Related Art

The human nervous system (HNS) includes the brain and the spinal cord, collectively known as the central nervous system (CNS). The central nervous system comprises nerve fibers that transmit nerve signals to, from, and within the brain and spinal cord. The network of nerves in the remaining portions of the human body forms the peripheral nervous system (PNS). Some peripheral nerves, known as cranial nerves, connect directly to the brain to control various brain functions, such as vision, eye movement, hearing, facial movement, and feeling. Another system of peripheral nerves, known as the autonomic nervous system (ANS), controls blood vessel diameter, intestinal movements, and actions of many internal organs. Autonomic functions include blood pressure, body temperature, heartbeat and essentially all the unconscious activities that occur without voluntary control.

Like the rest, of the human nervous system, nerve signals travel up and down the peripheral nerves, which link the brain to the rest of the human body. Many, but not all, nerve fibers, in the brain and the peripheral nerves are sheathed in a covering called myelin. The myelin sheath insulates electrical pulses traveling along the nerves. A nerve bundle may comprise up to 100,000 or more individual nerve fibers of different types, including larger diameter A and B fibers which comprise a myelin sheath and C fibers which have a much smaller diameter and are unmyelinated. Different types of nerve fibers, among other things, comprise different sizes, conduction velocities, stimulation thresholds, and myelination status (i.e., myelinated or unmyelinated).

More generally, the endogenous electrical activity (i.e., activity attributable to the natural functioning of the patient's own body) of a neural structure of a patient may be modulated in a variety of ways. In particular, the electrical activity may be modulated by exogenously applied (i.e., from a source other than the patient's own body) electrical, chemical, or mechanical signals applied to the neural structure.

The modulation of neural activity (hereinafter referred to generally as "neurostimulation" or "neuromodulation") may involve the application of an exogenous signal for the induction of afferent action potentials, efferent action potentials, or both, in the neural structure, and may also involve blocking or interrupting the transmission of endogenous electrical activity traveling along the nerve. Electrical neurostimulation or modulation of a neural structure refers to the application of an exogenous electrical signal (as opposed to a chemical or mechanical signal), to the neural structure. Electrical neurostimulation may be provided by implanting an electrical device underneath the skin of a patient and delivering an electrical signal to a nerve such as a cranial nerve. The electrical neurostimulation may involve performing a detection, with the electrical signal being delivered in response to a detected body parameter. This type of stimulation is generally referred to as "active," "feedback," or "triggered" stimulation. Alternatively, the system may operate without a detection system once the patient has been diagnosed with epilepsy (or another medical condition), and may periodically apply a series of electrical pulses to the nerve (e.g., a cranial nerve such as a vagus nerve) intermittently throughout the day, or over another predetermined time interval. This type of stimulation is generally referred to as "passive," "non-feedback," or "prophylactic," stimulation. The stimulation may be applied by an implantable medical device that is implanted within the patient's body.

The state-of-the-art also provides various methods for applying external signals to portions of a patient's body. An "external" signal, which may comprise an evoking signal and/or a therapeutic stimulation signal, refers to a signal delivered to the patient's body from a source outside the patient's body. The externally originating signal may, however, achieve its functional (e.g., stimulating and/or evoking) effect upon the target portion of the patient's body either internally or externally. For example, transcranial magnetic stimulation, an external signal, may be provided for internally stimulating various portions of the brain and/or cranial nerves. Further, external electrical stimulation may be provided by electrodes coupled to the patient's body externally. For example, electrodes coupled to various parts of a patient's face may stimulate various portions of the trigeminal nerve.

For many patients, the placement of the IMD, the associated electrodes and leads, in a particular location of the body may determine the efficacy of the neurostimulation delivered by the IMD. In some patients, neurostimulation of the left vagus nerve may be less effective than the neurostimulation provided to the right vagus nerve, or vice versa. This knowledge may be helpful in determining whether to implant the IMD on the right side or the left side of the patient, or on both left and right sides. The state-of-the-art generally lacks an effective manner of determining which side of a patient's body would be more conducive to stimulation from an IMD. More generally, effective screening methods are needed to assist in identifying, prior to implantation, those patients who are potential responders to neurostimulation therapy.

Additionally, different patients may exhibit dissimilar reactions to stimulation provided by the IMD. Generally, physicians estimate the value of various parameters (e.g., such as the amplitude, pulse widths, time periods between stimulation, etc.,) when determining the type of therapeutic signal to be used for stimulation. These estimates may be based upon prior experience with other patients and may not be optimum for other patients. Therefore, the physicians have to wait to analyze the results of the neurostimulation before assessing whether a current set of stimulation parameters are appropriate for a particular patient. However, analyzing the results of a therapeutic stimulation regimen may be a long-term process when studying the effectiveness of the treatment. Valuable treatment opportunities, and time, may be lost due to a time-lag in determining whether particular stimulation parameters being employed in an IMD is indeed effective. Therefore, the recovery or the attenuation of a particular disorder may be delayed using the state-of-the-art processes for determining the effectiveness of a particular set of stimulation parameters.

The present invention is directed to overcoming, or at least reducing, the effects of one or more of the problems set forth above.

SUMMARY OF THE INVENTION

In one aspect, the present invention comprises a method for affecting a neuromodulation based upon an external evoking signal applied to a patient's body. The method comprises applying an external evoking signal to a first target portion of a patient's body. Data relating to a physiological response resulting from applying the external evoking signal to the patient's body is received. The evoked physiological response may comprise one or more of a sensory response, a motor response, a visceral response, an autonomic response, and a somatosensory response. A neurotransmission characteristic of the patient's body is determined based upon the data relating to the physiological response. At least one parameter defining a therapeutic electrical stimulation signal provided by an implantable medical device is controlled based upon the neurotransmission characteristic to treat a disorder.

In another aspect, the present invention comprises a method for affecting a neuromodulation based upon an external evoking signal applied to a patient's body. An external evoking signal is applied to a first target portion of a patient's body. Data relating to a physiological response resulting from applying the external evoking signal to the patient's body is received. A neurotransmission characteristic of the patient's body is determined based upon the data relating to the physiological response. A determination is made as to a cranial nerve location or a cervical nerve location at which to couple an electrode for delivering a therapeutic electrical stimulation signal based on the neurotransmission characteristic.

In yet another aspect, the present invention comprises a method for identifying a patient as a candidate for a neurostimulation therapy based upon an external evoking signal applied to the patient's body. An external evoking signal is applied to a first target portion of a patient's body. Data relating to a physiological response resulting from applying the external evoking signal to the patient's body is received. A neurotransmission characteristic of the patient's body is determined based upon the data relating to the physiological response. A determination is made as to whether the patient is a potential candidate for a neurostimulation therapy based on the neurotransmission characteristic.

In another aspect, the present invention comprises a method for controlling a therapeutic neurostimulation signal provided by an implantable medical device based upon an external signal applied to the patient's body. A first signal from a source external to the implantable medical device is applied to a portion of a patient's body. Data relating to a physiological response resulting from the first signal is received. A neurotransmission characteristic of the patient's body is determined based upon the data relating to the physiological response. At least one parameter defining a therapeutic stimulation signal provided by the implantable medical device is adjusted based upon the neurotransmission characteristic to treat a disorder.

In yet another aspect, the present invention comprises a medical device system for providing neurostimulation therapy. The medical device system comprises at least one external stimulation system for delivering a first evoking signal to a first portion of a patient's body. The medical device system includes at least one implantable medical device (IMD) for delivering a therapeutic electrical signal to a second portion of the patient's body. The IMD includes a controller to receive data relating to a physiological response resulting from the first evoking signal. The controller is also adapted to determine a neurotransmission characteristic of the patient's body based upon the data relating to the physiological response, and to control at least one parameter defining the therapeutic electrical signal based upon the neurotransmission characteristic to treat a disorder.

In another aspect, the present invention comprises a method for treating a neurological disorder and/or a neuropsychiatric disorder using an implantable medical device. An evoking signal comprising a sensory stimulus, a visceral stimulus, a motor stimulus, an autonomic nervous system stimulus and/or a somatosensory stimulus is provided to a portion of a patient's body using a device external to the patient's body. A physiological response to the evoking signal is detected. A determination is made as to whether a parameter related to the physiological response exceeds a target value. A neuromodulation signal is provided to a portion of a nerve of the patient using the implantable medical device based upon a determination that the parameter related to the physiological response exceeds the target value.

In yet another aspect, the present invention comprises a method for performing an adaptive adjustment of a stimulation parameter of an implantable medical device. An evoking signal is delivered to a first portion of the patient's body using the implantable medical device. A physiological response to the evoking signal is sensed. At least one parameter relating to a therapeutic neuromodulation signal provided by the implantable medical device is adjusted based upon the physiological response to the evoking signal.

BRIEF DESCRIPTION OF THE DRAWINGS

The invention may be understood by reference to the following description taken in conjunction with the accompanying drawings, in which like reference numerals identify like elements, and in which:

FIGS. 7A, 7B, and 7C illustrate exemplary waveforms for generating the electrical signals for stimulating the vagus nerve for treating a neurological or neuropsychiatric disorder, according to one illustrative embodiment of the present invention;

Figure 1A:
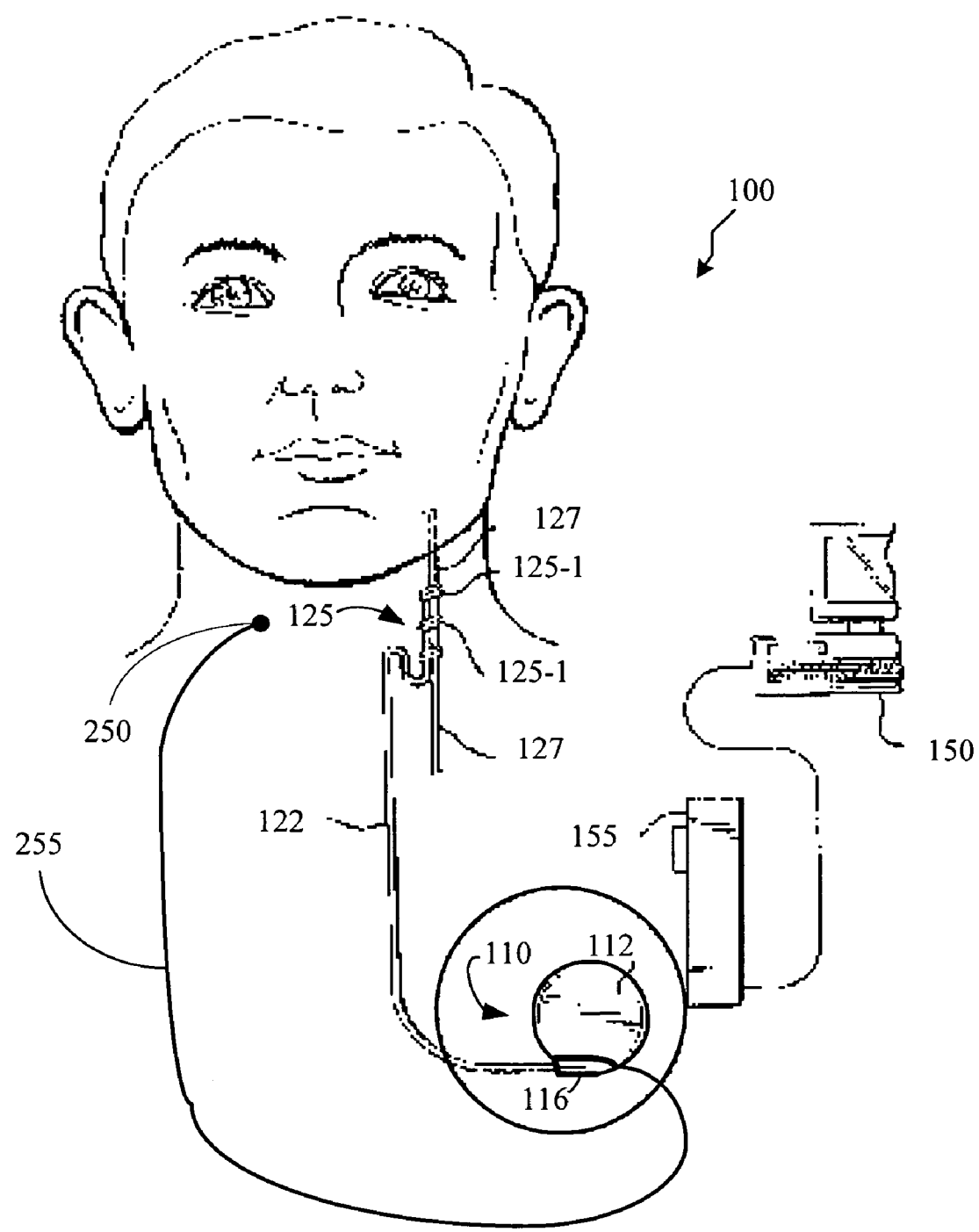
FIGS. 1A-1D provide stylized diagrams of an implantable medical device implanted into a patient's body for providing stimulation to a portion of the patient's body, in accordance with one illustrative embodiment of the present invention.
Figure 1B:
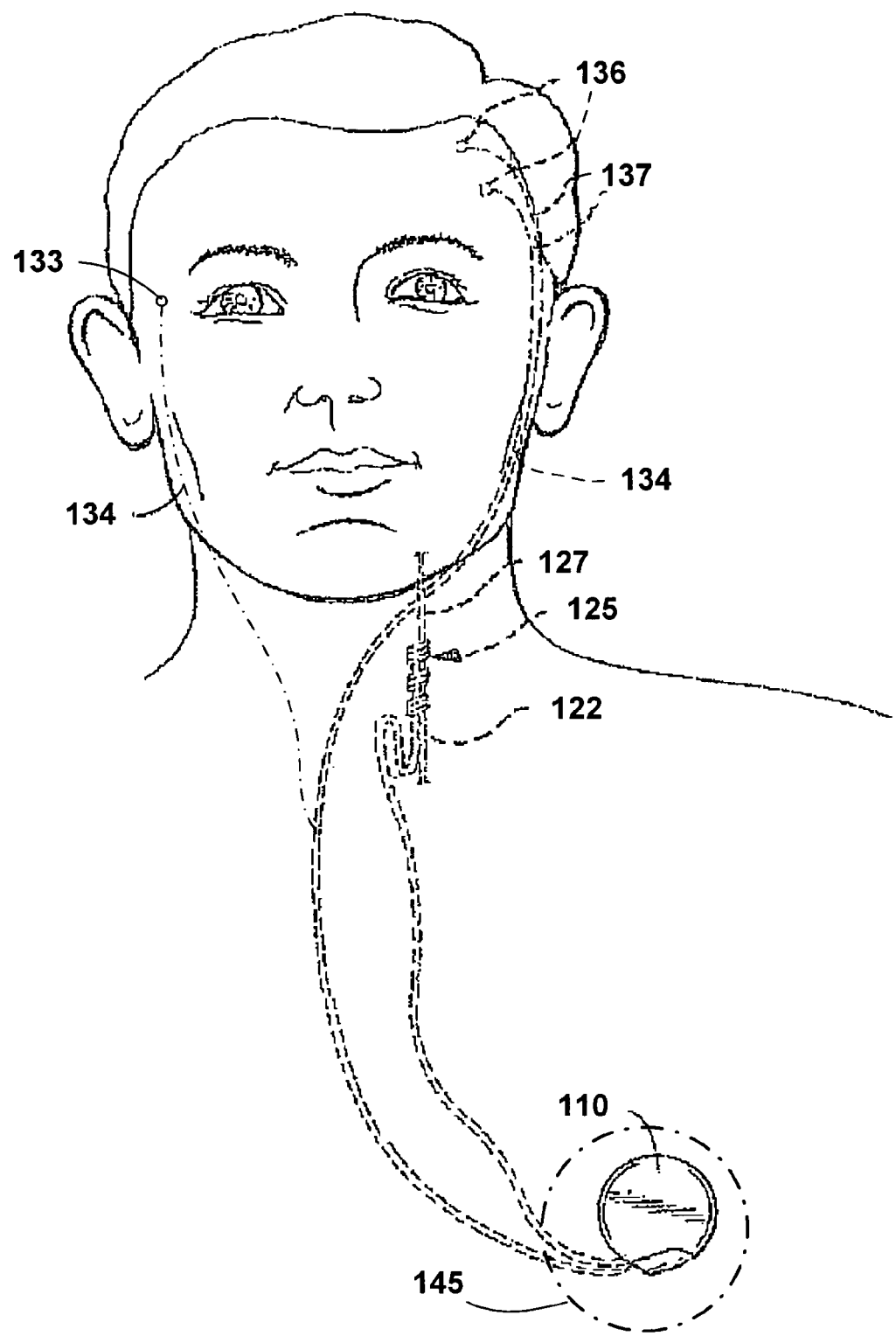
Figure 1C:
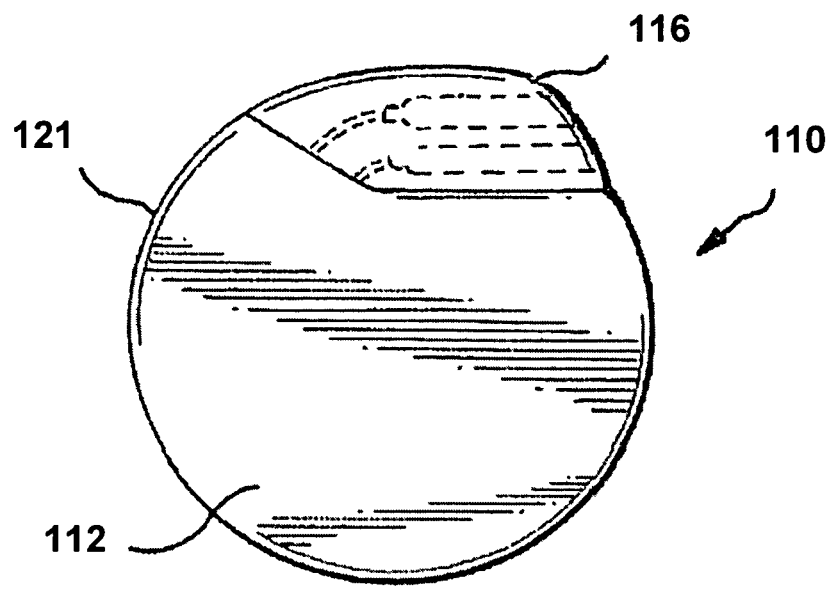

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

Certain terms are used throughout the following description and claims refer to particular system components. As one skilled in the art will appreciate, components may be referred to by different names. This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. For example, if a first device couples to a second device, that connection may be through a direct electrical connection or through an indirect electrical connection via other devices, biological tissues, or magnetic fields. "Direct contact," "direct attachment," or providing a "direct coupling" indicates that a surface of a first element contacts the surface of a second element with no substantial attenuating medium therebetween. The presence of substances, such as bodily fluids, that do not substantially attenuate electrical connections does not vitiate direct contact. The word "or" is used in the inclusive sense (i.e., "and/or") unless a specific use to the contrary is explicitly stated.

As used herein, "stimulation" or "stimulation signal" refers to the application of an electrical, mechanical, magnetic, electro-magnetic, photonic, audio and/or chemical signal to a neural structure in the patient's body. In one embodiment, the stimulation comprises an electrical signal. The stimulation signal may induce afferent and/or efferent action potentials on the nerve, may block native afferent and/or efferent action potentials, or may be applied at a sub-threshold level that neither generates action potentials nor blocks native action potentials. In one embodiment, the stimulation signal is a signal that is capable of inducing afferent and/or efferent action potentials on the nerve.

The stimulation signal applied to the neural structure in embodiments of the present invention refers to an exogenous signal that is distinct from the endogenous electrical, mechanical, and chemical activity (e.g., afferent and/or efferent electrical action potentials) generated by the patient's body and environment. In other words, the stimulation signal (whether electrical, mechanical, magnetic, electro-magnetic, photonic, audio or chemical in nature) applied to the nerve in the present invention is a signal applied from an artificial source, e.g., a neurostimulator.

As used herein, the terms "stimulating" and "stimulator" may generally refer to delivery of a stimulation signal to a neural structure. The effect of such stimulation on neuronal activity is termed "modulation"; however, for simplicity, the terms "stimulating" and "modulating", and variants thereof, are sometimes used interchangeably herein. In general, however, the delivery of an exogenous signal refers to "stimulation" of the neural structure, while the effects of that signal, if any, on the electrical activity of the neural structure are properly referred to as "modulation." The effect of delivery of the stimulation signal to the neural tissue may be excitatory or inhibitory and may potentiate acute and/or long-term changes in neuronal activity. For example, the "modulating" effect of the stimulation signal to the neural tissue may comprise one more of the following effects: (a) changes in neural tissue to initiate an action potential (bi-directional or uni-directional); (b) inhibition of conduction of action potentials (endogenous or externally stimulated) or blocking the conduction of action potentials (hyperpolarizing or collision blocking), (c) affecting changes in neurotransmitter/neuromodulator release or uptake, and (d) changes in neuro-plasticity or neurogenesis of brain tissue.

As used herein, the term "evoking signal" refers to a signal applied to a patient's body, through a stimulus modality acting internal or external to the patient's body, and it is intended to evoke a physiological response in the patient. The evoking signal may be delivered through any one or more of several modalities including but not limited to electrical, mechanical, magnetic, electro-magnetic, photonic, audio and/or chemical means. Examples of devices or equipment that may be used to provide an evoking signal to a patient's body includes but are not limited to the following: an implantable nerve stimulation medical device, a transcranial magnetic stimulator, a transcutaneus stimulation system, electromyography equipment, a drug pump, an audio sound-emitting device, a light-emitting device, standard neurological tests, a biothesiometer, etc. Typically, an evoked signal causes a rapid physiological response on the order of less than 1 second, however it is envisioned that some physiological responses could occur in a time frame longer than 1 second.

As used herein, the terms "therapeutic signal", "therapeutic stimulation signal" and variants thereof, are sometimes used interchangeably herein. Each refers to the signal delivered to a patient's body with the intent of treating a disorder by providing a modulating effect to neural tissue. This is in contrast to the term "evoking signal" which as defined above is intended to evoke a physiological response in the patient.

Embodiments of the present invention provides for adjusting at least one parameter of a therapeutic stimulation signal generated by an implantable medical device using results of an external and/or internal stimulus delivered to a portion of a patient's body. Cranial nerve stimulation has been proposed to treat a number of nervous system disorders, including epilepsy and other movement disorders, mood and other neuropsychiatric disorders, dementia, coma, migraine headache, obesity, eating disorders, sleep disorders, cardiac disorders (such as congestive heart failure and atrial fibrillation), hypertension, endocrine disorders (such as diabetes and hypoglycemia), and pain, among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the recognition that cranial nerve stimulation may be an appropriate treatment for the foregoing conditions, the fact that detailed neural pathways for many (if not all) cranial nerves remain relatively unknown makes predictions of efficacy for any given disorder difficult. Even if such pathways were known, moreover, the precise stimulation parameters that would energize particular pathways that affect the particular disorder likewise are difficult to predict.

In one embodiment of the present invention, methods, apparatus, and systems stimulate an autonomic nerve, such as a cranial nerve, e.g., a vagus nerve, using an electrical signal to treat an eating disorder. "Electrical signal" on the nerve refers to the electrical activity (i.e., afferent and/or efferent action potentials) that is not generated by the patient's body and environment, but is instead applied from an artificial source, e.g., an implanted neurostimulator. Disclosed herein is a method for treating an eating disorder using stimulation of the vagus nerve (cranial nerve X). Other types of eating disorders include, but are not limited to, bulimia nervosa, anorexia nervosa, compulsive and binge eating, and obesity. Bulimia nervosa ("bulimia") is an eating disorder in which an individual experiences recurrent episodes of insatiable craving for food often resulting in episodes of binge eating followed by inappropriate compensatory behavior to prevent weight gain. The inappropriate compensatory behavior typically includes self-induced vomiting, fasting, excessive exercise, and use of laxatives and diuretics. People suffering from bulimia commonly engage in binge eating and inappropriate compensatory behavior an average of two times a week for a period of three or more months. Treatments to address these disorders include physiological treatments, as well as psychological and psychiatric treatments. Besides drug regimens, invasive medical procedures, and/or counseling, effective treatment of such diseases and disorders are somewhat limited. Further, certain patients may not react favorably to various types of drugs or other treatments. A generally suitable form of neurostimulator for use in the method and apparatus of the present invention is disclosed, for example, in U.S. Pat. No. 5,154,172, assigned to the same assignee as the present application. The neurostimulator may be referred to a NeuroCybernetic Prosthesis (NCP®, Cyberonics, Inc., Houston, Tex. the assignee of the present application). Certain parameters of the electrical stimulus generated by the neurostimulator are programmable, such as be means of an external programmer in a manner conventional for implantable electrical medical devices.

In one embodiment, treatment of neuropsychiatric mood disorders is proposed. Mood disorders for which treatment is contemplated include, but are not limited to, depression, major depressive disorder, bipolar disorder, dysthymic disorder, anxiety disorders. Anxiety disorders include, but are not limited to, obsessive compulsive disorder (OCD), post-traumatic stress syndrome (PTSD), panic disorder, generalized anxiety, simple phobia and social phobia. For ease of reference, the use of the term "mood disorder" herein also includes the above-named disorders.

Yet another embodiment includes treatment of a disorder of the endocrine stress system. This includes disorders associated with the hypothalmus-pitituary-adrenal (HPA) axis and sympathetic-adrenal medullary (SAM) axis and includes, but is not limited to, disorders of the hormone system, energy metabolism-related disorders, and reproductive disorders.

Embodiments of the present invention provide for an adaptive or feedback type adjustment of stimulation parameters for providing a therapeutic stimulation (e.g., neurostimulation) using an implantable medical device (IMD). An evoking signal may be applied using one or more external stimulation sources, one or more internal stimulation source (internal to the patient's body), and/or a combination of the internal and external sources.

An external evoking signal may be provided to a patient and the results of the external evoking signal may be analyzed. The external evoking signal may include various types of stimulation techniques, such as a transcranial stimulation or other type of external evoking signal, such as electrical stimulation delivered through an electrode, an auditory stimulation, a visual stimulation, an evoked potential, etc. The external evoking signal may also refer to an externally applied stimulus that acts to achieve its evoked response internally. The may be a result of a signal that is exogenously applied (i.e., from a source other than the patient's own body) electrical, chemical, auditory, visual, and/or mechanical signals applied to the neural structure. The results of the external evoking signal may be examined to determine various factors that may be used to adjust internal stimulation parameters (i.e., parameters used by the IMD to generate stimulation signals). For example, the latency relating to the reaction in the patient's body due to an external evoking signal may be analyzed. This latency analysis may be initiated by various stimulation techniques, such as external stimulation that may be provided to induce a neuro-response, such as a somatosensory and/or a motor sensory response. This latency relating to the neuro-response may be logged and/or compared to a predetermined tabulated set of data that provides correlation between various stimulation parameters and particular expected latencies. The latencies or other indications resulting from the response to the external evoking signal may provide indications of neuro-pathway efficiency in a particular patient. Based upon a patient's response to external evoking signal, various adjustments to the stimulation parameter for delivering an internal stimulation may be performed.

Embodiments of the present invention also provide for analyzing the efficiency of the neuro-pathways of various portions of the patient's body. For example, respective factors relating to the left vagus nerve transmission may be compared to factors relating to the right vagus nerve transmission to determine whether the implantable medical device should be implanted in the right side or the left side of the patient's body.

Further, embodiments of the present invention provide for performing an adaptive adjustment of therapeutic stimulation parameters based upon the resultant physiological response due to internal evoking signal (i.e., evoking signal provided by a source inside the patient's body). For example, upon delivery of an internal evoking signal, various physiological responses may be measured. A process for examining the physiological factors may include recording, measuring, sensing, monitoring, and/or analyzing physiological data. The physiological factors relating to the internal evoking signal may be compared with baseline values, reference values, and/or expected values of various physiological responses. Based upon this response, an adaptive adjustment to the stimulation parameters may be performed for the subsequent delivery of a therapeutic stimulation for treating a disorder. This adaptive process may be repeated in a predetermined fashion or in an automated fashion wherein the adaptive adjustment process is continuously performed by the IMD. In this manner, more effective delivery of therapeutic stimulation that is more tailored to a particular patient may be provided. Embodiments of the present invention may provide for improving the efficacy and the effectiveness of neurostimulation.

The evoking signal (whether provided by an internal or an external signal) may refer to one or more of a number of stimulus modalities. The various modalities may include number of diagnostic methods where a stimulus is applied to the body, such as an auditory modality prompting audio evoked responses, a sensory evoking modality, a somatosensory evoking modality, an autonomic nervous system evoking modality, a motor or neuromuscular evoking modality, a somatosensory modality relating to a brainstem somatosensory evoked responses (BSER), a visual system evoking modality, etc.

Although not so limited, a system capable of implementing embodiments of the present invention is described below. FIGS. 1A-1D depict a stylized implantable medical system 100 for implementing one or more embodiments of the present invention. FIGS. 1A-1D illustrate an electrical signal generator 110 having main body 112 comprising a case or shell 121 (FIG. 1A) with a header 116 (FIG. 1C) for connecting to leads 122. The generator 110 is implanted in the patient's chest in a pocket or cavity formed by the implanting surgeon just below the skin (indicated by a dotted line 145, FIG. 1B), similar to the implantation procedure for a pacemaker pulse generator.

Figure 1D:
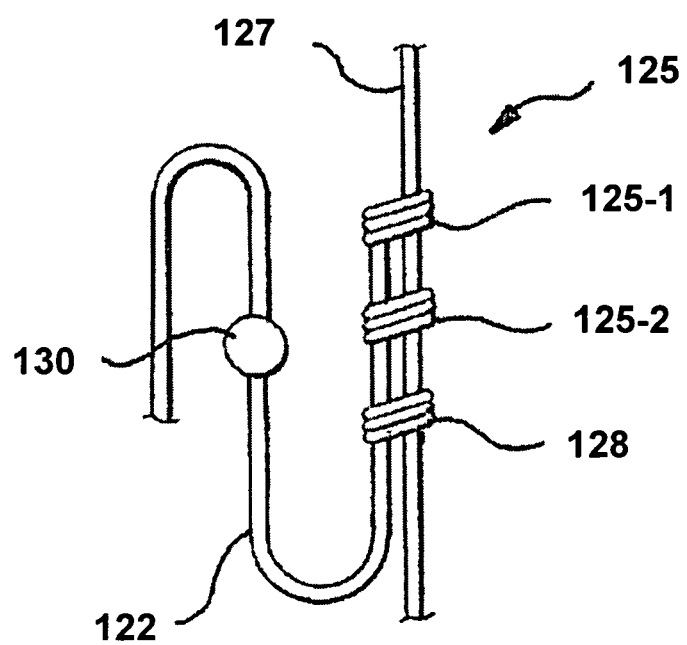

A stimulating nerve electrode assembly 125, preferably comprising an electrode pair, is conductively connected to the distal end of an insulated, electrically conductive lead assembly 122, which preferably comprises a pair of lead wires (one wire for each electrode of an electrode pair). Lead assembly 122 is attached at its proximal end to connectors on the header 116 (FIG. 1C) on case 121. The electrode assembly 125 may be surgically coupled to a vagus nerve 127 in the patient's neck or at another location, e.g., near the patient's diaphragm. Other cranial nerves may also be used to deliver the electrical neurostimulation signal and/or an evoking signal. The electrode assembly 125 preferably comprises a bipolar stimulating electrode pair 125-1, 125-2 (FIG. 1D), such as the electrode pair described in U.S. Pat. No. 4,573,481 issued Mar. 4, 1986 to Bullara. Suitable electrode assemblies are available from Cyberonics, Inc., Houston, Tex., USA as the Model 302 electrode assembly. However, persons of skill in the art will appreciate that many electrode designs could be used in the present invention. The two electrodes are preferably wrapped about the vagus nerve, and the electrode assembly 125 may be secured to the nerve 127 by a spiral anchoring tether 128 (FIG. 1D) such as that disclosed in U.S. Pat. No. 4,979,511 issued Dec. 25, 1990 to Reese S. Terry, Jr. and assigned to the same assignee as the instant application. Lead assembly 122 is secured, while retaining the ability to flex with movement of the chest and neck, by a suture connection 130 to nearby tissue (FIG. 1D).

In one embodiment, the open helical design of the electrode assembly 125 (described in detail in the above-cited Bullara patent), which is self-sizing and flexible, minimizes mechanical trauma to the nerve and allows body fluid interchange with the nerve. The electrode assembly 125 preferably conforms to the shape of the nerve, providing a low stimulation threshold by allowing a large stimulation contact area with the nerve. Structurally, the electrode assembly 125 comprises two electrode ribbons (not shown), of a conductive material such as platinum, iridium, platinum-iridium alloys, and/or oxides of the foregoing. The electrode ribbons are individually bonded to an inside surface of an elastomeric body portion of the two spiral electrodes 125-1 and 125-2 (FIG. 1D), which may comprise two spiral loops of a three-loop helical assembly. The lead assembly 122 may comprise two distinct lead wires or a coaxial cable whose two conductive elements are respectively coupled to one of the conductive electrode ribbons. One suitable method of coupling the lead wires or cable to the electrodes 125-1, 125-2 comprises a spacer assembly such as that disclosed in U.S. Pat. No. 5,531,778, although other known coupling techniques may be used.

The elastomeric body portion of each loop is preferably composed of silicone rubber, and the third loop 128 (which typically has no electrode) acts as the anchoring tether for the electrode assembly 125.

In certain embodiments of the invention, sensors such as eye movement sensing electrodes 133 (FIG. 1B) may be implanted at or near an outer periphery of each eye socket in a suitable location to sense muscle movement or actual eye movement. The electrodes 133 may be electrically connected to leads 134 implanted via a cannula or other suitable means (not shown) and extending along the jaw line through the neck and chest tissue to the header 116 of the electrical pulse generator 110. When included in systems of the present invention, the sensing electrodes 133 may be utilized for detecting rapid eye movement (REM) in a pattern indicative of a disorder to be treated. The detected indication of the disorder can be used to trigger active stimulation.

Other sensor arrangements may alternatively or additionally be employed to trigger active stimulation and/or to detect a physiological response to an evoking signal. Referring again to FIG. 1B, electroencephalograph (EEG) sensing electrodes 136 may optionally be implanted and uniformly distributed on the skull, and connected to leads 137 implanted and extending along the scalp and temple, and then connected to the electrical pulse generator 110 along the same path and in the same manner as described above for the eye movement electrode leads 134.

In alternative embodiments, temperature sensing elements and/or heart rate sensor elements may be employed to trigger active stimulation. In addition to active stimulation incorporating sensor elements, other embodiments of the present invention utilize passive stimulation to deliver a continuous, periodic or intermittent electrical signal (each of which constitutes a form of continual application of the signal) to the vagus nerve according to a programmed on/off duty cycle without the use of sensors to trigger therapy delivery. Both passive and active stimulation may be combined or delivered by a single IMD according to the present invention. Either or both modes may be appropriate to treat the particular disorder diagnosed in the case of a specific patient under observation.

The electrical pulse generator 110 may be programmed with an external computer 150 using programming software of the type copyrighted by the assignee of the instant application with the Register of Copyrights, Library of Congress, or other suitable software based on the description herein, and a programming wand 155 to facilitate radio frequency (RF) communication between the computer 150 (FIG. 1A) and the pulse generator 110. The wand 155 and software permit non-invasive communication with the generator 110 after the latter is implanted. The wand 155 is preferably powered by internal batteries, and provided with a "power on" light to indicate sufficient power for communication. Another indicator light may be provided to show that data transmission is occurring between the wand and the generator.

A variety of stimulation therapies may be provided in implantable medical systems 100 of the present invention. Different types of nerve fibers (e.g., A, B, and C fibers being different fibers targeted for stimulation) respond differently to stimulation from electrical signals. More specifically, the different types of nerve fibers have different conduction velocities and stimulation thresholds and, therefore, differ in their responsiveness to stimulation. Certain pulses of an electrical stimulation signal, for example, may be below the stimulation threshold for a particular fiber and, therefore, may generate no action potential in the fiber. Thus, smaller or narrower pulses may be used to avoid stimulation of certain nerve fibers (such as C fibers) and target other nerve fibers (such as A and/or B fibers, which generally have lower stimulation thresholds and higher conduction velocities than C fibers). Additionally; techniques such as pre-polarization may be employed wherein particular nerve regions may be polarized before a more robust stimulation is delivered, which may better accommodate particular electrode materials. Furthermore, opposing polarity phases separated by a zero current phase may be used to excite particular axons or postpone nerve fatigue during long term stimulation.

Figure 2:
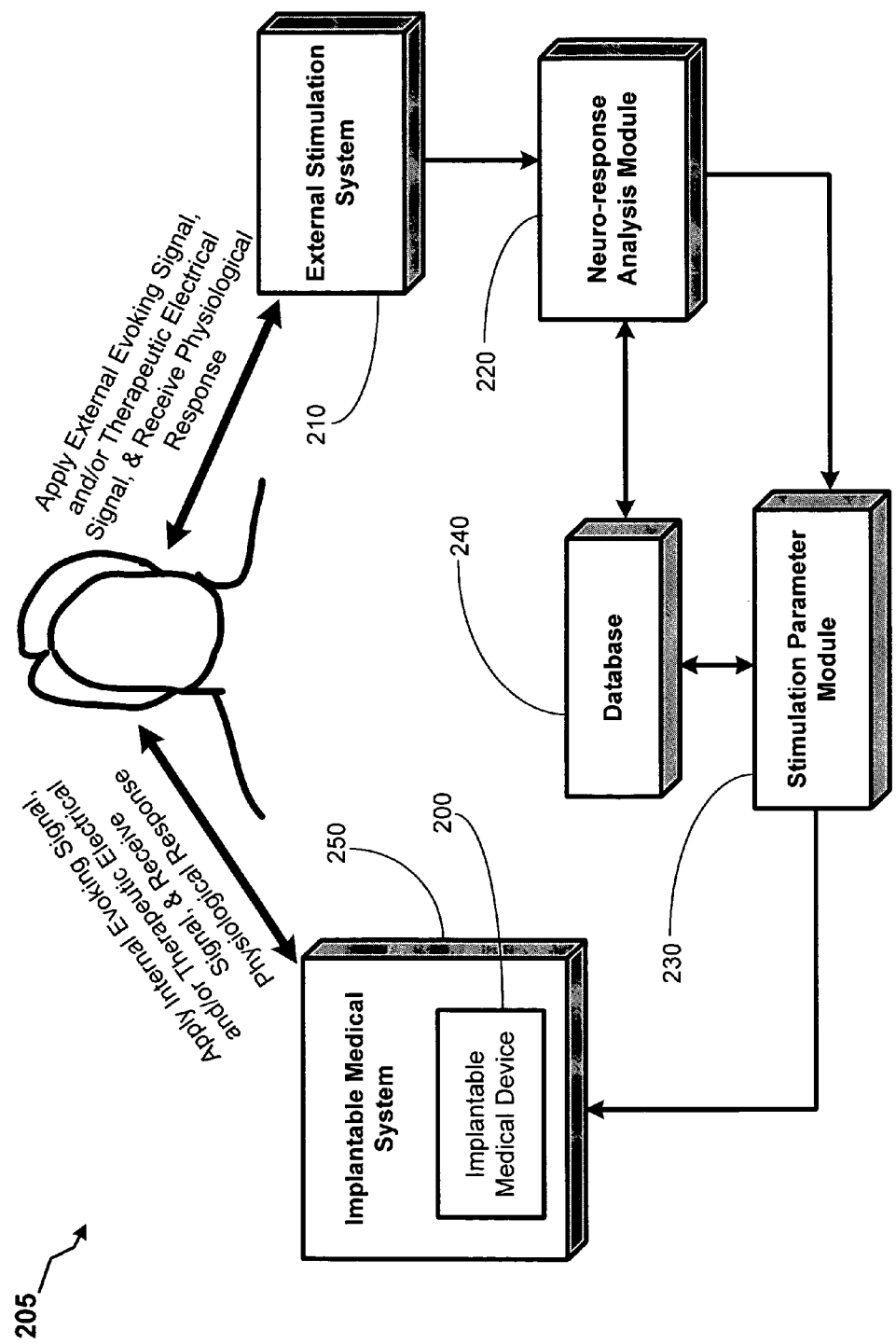
FIG. 2 provides a stylized depiction of a therapeutic system that includes an external stimulation system and an internal stimulation system, in accordance with one illustrative embodiment of the present invention.

Turning now to FIG. 2, a stylized diagram of a system 205 that includes an external stimulation system and an internal stimulation system to affect the therapeutic stimulation provided by implantable medical device is provided. Embodiments of the present invention provide for applying an external evoking signal. The system 205 may combine various elements related to an external evoking process, as well as a system related to an internal therapeutic stimulation and evoking process that includes an IMD. The external stimulation system 210 of FIG. 2 is capable of providing various types of therapeutic stimulation and/or evoking signals to a variety of portions of a patient's body. An example of the external stimulation system 210 may include a transcranial magnetic stimulation (TMS) system and/or various electrical stimulation systems. The external stimulation system 210 may comprise various electrodes and other signal discharge devices to provide an external stimulation.

Delivery of an external stimulation may evoke various types of responses in the patient's body. As used herein, the term "physiological response" refers to an evoked response to a stimulus signal or to an evoking signal. Several types of physiological responses, such as somatosensory responses, motor responses, neuro-responses and/or cortical responses, etc., may be prompted by the external stimulation. Based upon the external evoking signal provided to the patient, data relating to various physiological responses may be received by the external stimulation system 210. The external stimulation result data may then be recorded for further analysis. Further details as to a first embodiment and a second embodiment of the external stimulation system 210 are provided in FIGS. 3 and 4, as well as the accompanying description below.

The system 205 may also comprise a neuro-response analysis module 220. The neuro-response analysis module 220 may analyze various neurological responses (e.g., somatosensory responses, visceral responses, motor responses, cortical responses, and/or any other types of neurological responses) resulting from the external evoking signal. The analysis of the physiological responses due to the external evoking process may be correlated to various physiological factors associated with a patient (e.g., the patient's disorder, physical characteristics, etc.). Further, the analysis provided by the neuro-response analysis module 220 may provide indications of various neuro-transmission characteristics or factors associated with a particular patient's body. This may provide an indication as to the types of signals provided by an implantable medical device that would be more effective for a particular patient. Neuro-transmission characteristics may include, but not be limited to, a time delay between delivery of a evoking signal and a physiological response, the magnitude of a physiological response signal, a frequency of a physiological response signal, a conduction velocity of an evoked response signal, a signal latency, and a spectral analysis characteristic of a stimulus response signal. Other neuro-transmission characteristics or factors may be those derived from nerve conduction tests such as the f-wave and h-reflex response. Parameters associated with measurements of somatosensory evoked potentials including onset latency, inter-peak latency, morphology (i.e., presence and absence of components), polarity, and dispersion. EEG or evoked potential recording electrodes can be placed on the head or body to record the neurotransmission characteristics. Several types of well known neurological tests involve measurement of evoked potentials and these tests include Brainstem Auditory Evoked Potential (BAEP), Somatosensory Evoked Potential (SSEP) and Visual Evoked Potential (VEP).

One example of a physiological response to external stimulation is a cortical response that includes a combination of a somatosensory response and a motor response. Examples of cortical responses may include performing a frontal cortex stimulation (e.g., transcranial magnetic stimulation) that may provide a combination of a somatosensory and a motor response. For example, based upon the delivery of frontal cortex stimulation, some patients may exhibit a response characterized by a predictable movement of a finger (e.g., movement of the thumb or the index finger). For example, certain frontal cortex stimulations may prompt the thumb or the index finger of the patient to close, or to activate the patient's contralateral first dorsal interosseous muscle (FDI). This response may be conducted through motor as well as a somatosensory neural pathway.

Analyzing the physiological responses may provide an indication of latency between the time that the external stimulation signal is applied and the time of the occurrence of the response. Therefore, the exemplary frontal cortex stimulation described above and the movement of the thumb in response, may provide a latency calculation relating to a neuro-transmission factor of a particular patient.

This data may then be used to initially, or adaptively, adjust various stimulation parameters. Further, examples of providing an external stimulation and measuring the effects may include providing a contra-lateral effect test. An example of a contra-lateral test may be the blink test. For example, in this test the trigeminal or facial nerves are electrically stimulated resulting in reflex contraction of the orbicularis oculi. The blink reflex is a central nervous system effect and the latencies of the ipsilateral side of the face can be of shorter duration than the contralateral side. The latency time difference of the eye-blinking response is a function of neural conduction and synaptic transmission. By correlating differences in synaptic transmission rate to the IMD treatment parameters, it may be possible to optimize the IMD stimulation treatment parameters. Latency relating to the blink test may also be recorded for use in adjustments of stimulation parameters relating to neurostimulation provided by the IMD 200.

The system 205 may also provide an implantable medical system 250, which is capable of applying internal stimulus and therapeutic stimulation provided internally into the patient's body. The implantable medical system 250 comprises various components illustrated in FIGS. 1A-1D, which may include an implantable medical device (IMD) 200, an external device (described in FIG. 8 and accompanying description below) to program and effect the operation of the IMD 200. The IMD 200 may comprise a pulse generator located external to the patient's body, coupled to an implanted stimulating electrode via a wireless link or through a primary coil adapted to be coupled with a subcutaneous secondary coil of an implanted receiving means for neuromodulation treatment.

The system 205 may also comprise a database 240 that may provide a tabulation of various patient characteristics to particular neuro-transmission parameters. Consultation into the database 240 may provide correlation between the types of internal stimulation that may be desirable based upon various physiological parameters of a particular patient. A stimulation parameter module 230 in FIG. 2, may be capable of accessing data from the database 240 based upon data received from the neuro-response analysis module 220. Based upon such correlation, various components of the implantable medical system 250 may be programmed or reprogrammed to affect the operation of the therapeutic stimulation and/or evoking signals provided by the IMD 200. Therefore, various physiological responses due to an external stimulation may be used to adaptively affect the operation of an IMD 200 when delivering internal stimulation.

The external and internal stimulation systems 210, 250 may provide numerous types of evoking signals and/or therapeutic signals using various types of stimulation. The external and internal stimulation systems 210, 250 may deliver a therapeutic electrical stimulus to at least one cranial nerve and/or a sympathetic nerve. This process may also be used for brain stimulation (e.g., cortical, dural, subdural, deep-brain). In one embodiment, the therapeutic stimulation signal may be provided by a spinal cord stimulation system. The external and internal stimulation systems 210, 250 may provide evoking signals and/or therapeutic signals with a variety of parameters, such as constant frequency, patterned, coded, one or more sequential pulses separated by an inter-pulse interval, and/or a series of pulses separated by a pulse train or duty cycle interval. Further, the pulse amplitude, frequency, pulse width, intensity, power, or charge/pulse may vary among the pulses, and the current or voltage amplitude can be of opposite polarity during any portion of the pulse train. Multiple pulse paradigms can be interleaved, synchronous or asynchronous. By using interleaved stimulation parameters, different frequency-dependent or network synapses may be modulated to achieve the effective treatment response.

Further, the external and internal stimulation systems 210, 250 may each represent a plurality of external and internal devices that are capable of delivering a plurality of external and internal therapeutic signals and/or evoking signals. Further, the device(s) within the external stimulation system 210 may be in communication (e.g., wireless communication and/or wired communication) with each other and/or with one or more devices associated with the internal stimulation system 250. Similarly, the device(s) within the internal stimulation system 250 may be in communication (e.g., wireless communication and/or wired communications) with each other and/or with one or more devices associated with the external stimulation system 210. In this manner, various external and internal therapeutic and/or evoking signals may be synchronized and coordinated. Further, the physiological results of the external and internal therapeutic and/or evoking signals may be shared by the external and internal stimulation systems 210, 250 for analysis to determine stimulation parameters relating to therapeutic stimulation.

Figure 3:
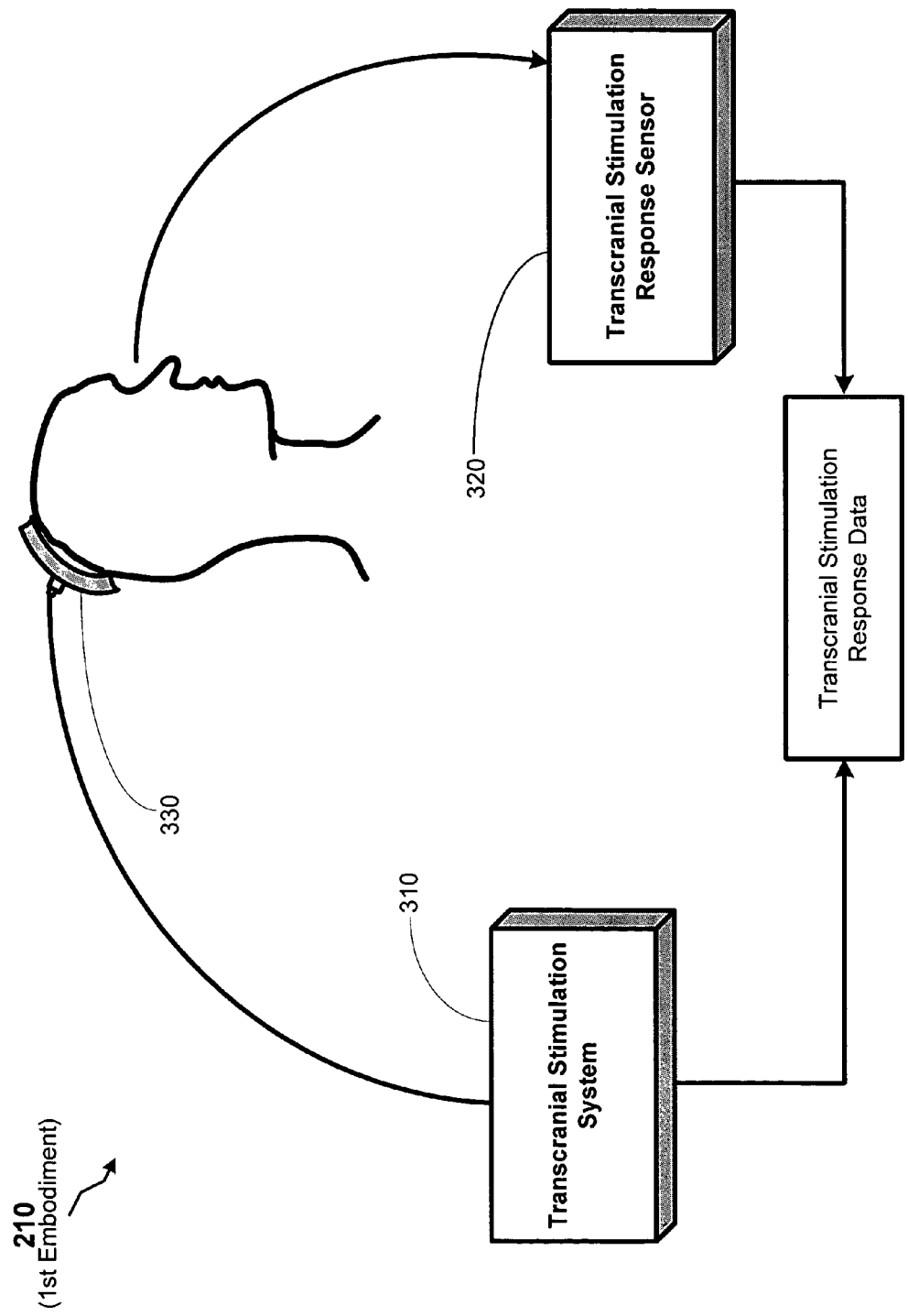
FIG. 3 provides a stylized depiction of a first embodiment of an external stimulation system of FIG. 2, in accordance with one illustrative embodiment of the present invention.

Turning now to FIG. 3, a stylized diagram of the external stimulation system 210, in accordance with a first embodiment of the present invention is depicted. FIG. 3 illustrates a transcranial stimulation system 310 that is capable of delivering transcranial stimulation to a portion of the patient's cerebral cortex or other neural structure. In one embodiment, the transcranial stimulation system 310 provides a magnetic transcranial stimulation to the patient. The transcranial stimulation system 310 may comprise various components that are capable of generating and providing stimulation signals, such as a magnetic or an electrical stimulation signal. The transcranial stimulation system 310 may then deliver the therapeutic signals and/or evoking signals to a portion of the patient's brain or other neural structure via a stimulation delivery component 330. The stimulation delivery component 330 may be capable of providing a magnetic field, an electrical field, and/or an electro-magnetic field. An electrical field as discussed herein could be performed by application of electro-convulsive therapy stimulation.

The external stimulation system 210 may also comprise a transcranial stimulation response sensor 320. The effect sensor 320 may comprise various circuitry and sensors that are capable of detecting responses, such as somatosensory responses, motor responses, cortical responses, visually evoked responses (VEP), auditory evoked potential (AEP), brainstem auditory evoked potentials (BSEP), and/or any type of neuro-response. The transcranial stimulation effect sensor 320 may detect various physiological responses and correlate them to the particular type of transcranial therapeutic signals and/or evoking signals that are delivered by the transcranial stimulation system 310. The transcranial stimulation effect sensor 320 may then tabulate and provide transcranial evoking signal response data to the system 205.

Figure 4:
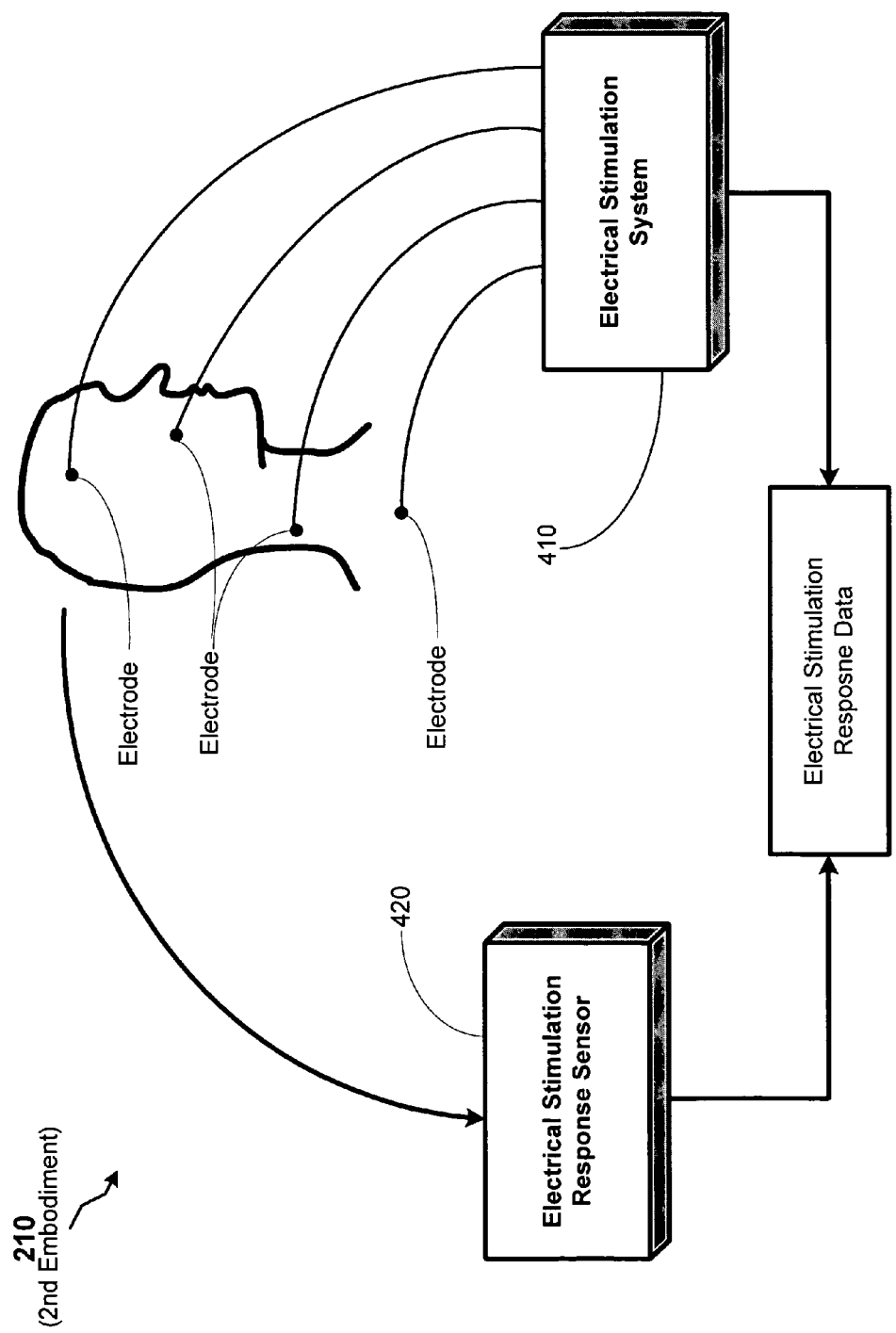
FIG. 4 provides a stylized depiction of a second embodiment of an external stimulation system of FIG. 2, in accordance with another illustrative embodiment of the present invention.

Turning now to FIG. 4, a stylized diagram of the external stimulation system 210 of FIG. 2, in accordance with a second illustrative embodiment of the present invention is provided. The embodiment of FIG. 4 may provide for externally delivering electrical therapeutic signals and/or evoking signals. The external stimulation system 210 of FIG. 4 may include an electrical stimulation system 410 that is capable of delivering therapeutic signals and/or evoking signals to various portions of the patient's body. The electrical stimulation system 210 may comprise various circuitry and devices to charge-up and deliver a predetermined amount of electric charge to an electrode that is attached to a portion of the patient's body. Various regions of the face, head, neck or other portions of the body may be stimulated externally.

The external stimulation system 210 of FIG. 4 may also comprise an electrical stimulation response sensor 420. The sensor 420 may include various sensors and circuitry that are capable of detecting various somatosensory, visceral, motor, cortical and/or other neuro-responses. The electrical stimulation effect sensor 420 is capable of correlating particular effects to particular therapeutic signals and/or evoking signals provided to the patient. Latency relating to the effects prompted by the delivery of electrical therapeutic signals and/or evoking signals may also be calculated and tabulated. The external stimulation system 210 then provides signal response data to the system 205 for further analysis, as illustrated in FIG. 4.

Figure 5:
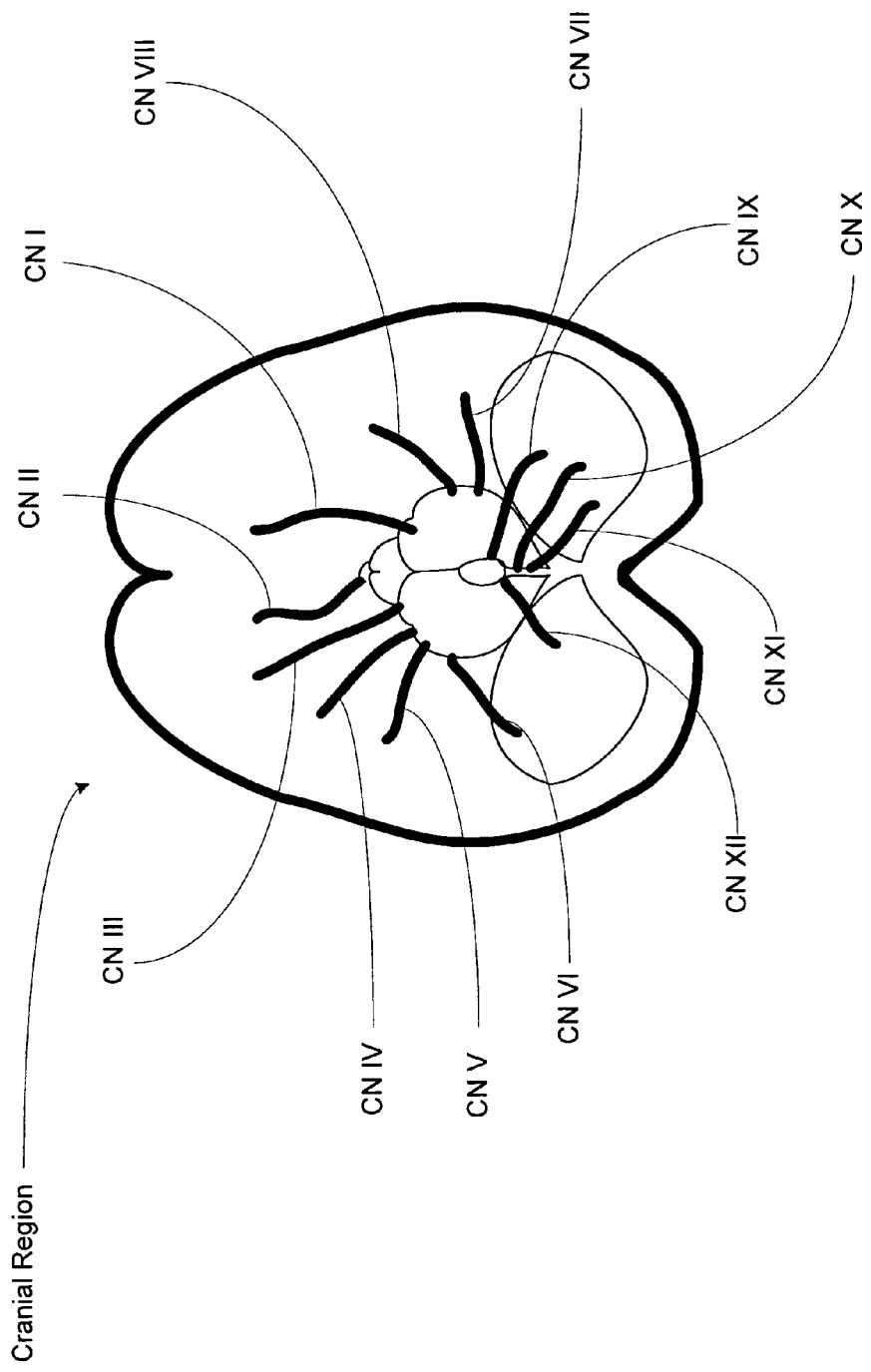
FIG. 5 depicts a stylized diagram of a transverse section of the brain stem showing various cranial nerves that could be affected by the internal and/or external stimulation provided by illustrative embodiments of the present invention.

FIG. 5 illustrates, in a stylized fashion, various cranial nerves that may be stimulated by the therapeutic signals and/or evoking signals provided by the external stimulation system 210, which may induce an effect for further analysis. Various effects relating to the cranial nerves may be measured and analyzed to determine a latency or other neuro-transmission characteristic(s) for a particular patient. This information may then be used to adjust various stimulation parameters relating to a therapeutic neurostimulation provided by the IMD 200.

Generally, the cranial nerves comprise a system of nerves that include ten basic cranial nerves, which branch into further sections and sub-sections. In one embodiment, the implantable medical system 250 and/or the external stimulation system 210 may target the stimulation of cranial nerve I (CN I). The cranial nerve 1 relates to the olfactory nerve, which is a special sensory nerve. The olfactory nerve is generally located in the olfactory epithelium and exits from the cranium from the foramina in the cribriform plate of the ethmoid bone. An external stimulation that targets CN 1 may produce an effect that includes a nasal response (e.g., a smell response) in a patient. A neuro-response test may be provided where the patient responds to an external and/or internal evoking signal by indicating the detection of nasal effect caused by the external stimulation. Latency relating to the time period of this effect may be measured. This latency may then be used to control various parameters of an internal stimulation provided by the IMD 200.

The implantable medical system 250 and/or the external stimulation system 210 may target cranial nerve II (CN II), which relates to the optic nerve. The optic nerve components are special sensory components, the cell bodies of which are located in the retina. CN II exits the cranial system via the optic canal. The external and/or internal evoking of the optic nerve may be detected by a patient via a vision response. This response may then be used to determine various neuro-transmission characteristics of a patient.

In yet another embodiment, the implantable medical system 250 and/or the external stimulation system 210 may target cranial nerve III (CN III), which relates to the oculomotor nerve. Cranial nerve III is a somatic motor component, wherein the location of its cell bodies is in the midbrain region. The oculomotor also has a visceral motor component as well, wherein the locations of its cell bodies are in the presynaptic midbrain region as well as in the postsynaptic ciliary ganglion. The cranial exit of the oculomotor nerve is via the superior orbital fissure. Various physiological responses resulting from an external and/or internal evoking signal sent to cranial nerve III may be measurable. These physiological responses may include a motor response of the eyelid and/or parasympathetic innervations of the pupil and the ciliary muscle, which may provide for a constriction of the pupil. These responses may be measured to determine a neuro-transmission characteristic of a particular patient, this information may then be used to generate and/or adjust the stimulation parameters for an internal therapeutic stimulation delivered by the IMD 200.

The implantable medical system 250 and/or the external stimulation system 210 may also target cranial nerve IV (CN IV), which relates to the trochlear nerve. Cranial nerve IV relates to a somatic motor component, the cell bodies of which are located in the midbrain. The cranial exit of CN IV is via the superior orbital fissure. Effects due to stimulation of CN IV may include a movement or turning of the eye inferolaterally, or turning of the eye inferiorly when adducted. The movement of the eye may then be measured relative to the time the external and/or internal evoking signal is sent to the CN IV is delivered, thereby calculating a latency or other neuro-transmission characteristics of a particular patient.

The implantable medical system 250 and/or the external stimulation system 210 may target cranial nerve V (CN V), i.e., the trigeminal nerve, relates to the ophthalmic nerve, the maxillary nerve, and the mandibular nerve. The trigeminal nerve has a general sensory component and its cell bodies are located in the trigeminal ganglion. The cranial exit of the trigeminal nerve is via the superior orbital fissure, the foramen rotundum, and the foramen ovale, respectively for the ophthalmic, the maxillary, and the mandibular nerve components. External and/or internal evoking signal sent to the trigeminal nerve may cause a resultant effect of a sensation from the cornea, skin of the forehead, the scalp, eyelids, nose, etc. Delivery of external and/or internal evoking signals to the trigeminal nerve may also prompt a sensation of the upper lip or the maxillary sinuses and palate. Further, CN V may also include a sensation in the majority of a portion of the tongue of the patient. These various physiological responses from the delivery of external and/or internal evoking signals to the CN V may then be used to determine the latency or other neuro-responses of a particular patient. The timing of various facial responses to the external and/or internal evoking signals may then be measured to calculate the latency or other neuro-transmission characteristics of the patient.

The implantable medical system 250 and/or the external stimulation system 210 of the present invention may also target cranial nerve VI (CN VI), which relates to the abducent nerve. Cranial nerve VI has a somatic motor component and is generally located in the pons. The exit of CN VI is via the superior orbital fissure. The physiological responses of the deliver of external and/or internal evoking signals to CN VI may be a lateral movement of the eye, which may be used to determine the neuro-transmission factors for a particular patient.

Further, the implantable medical system 250 and/or the external stimulation system 210 may also target the cranial nerve VII (CN VII), which relates to the facial nerves. Cranial nerve VII affects the facial muscles. The cranial nerve VII may be externally and/or internally evoked to prompt various external responses such as changes in facial expressions. Cranial nerve VII relates to a special sensory nerve and comprises various components, such as the bronchial motor and the visceral motor. Other physiological responses may relate to a taste response, as well as parasympathetic innervations, e.g., a parasympathetic innervations of the salivary glands. Based upon the neuro-transmission characteristics developed by the analysis response to the stimulation of CN VII, a latency or transmission characteristics of a particular patient may be determined.

The implantable medical system 250 and/or the external stimulation unit 210 may also target the cranial nerve VIII (CN VIII), which relates to the vestibulocochlear. The vestibulocochlear includes the vestibular nerve and the cochlear nerve. Cranial nerve VIII relates to special sensory components, for which the cell bodies are located in the vestibular ganglion and the spiral ganglion. The cranial exit of CN VIII is via the internal acoustic meatus. The physiological response due to an external and/or internal evoking signal sent to CN VIII may relate to a particular movement of the head that may be detected by the patient or a physician. The physiological response may also include a hearing sensation resulting from the external and/or internal evoking signals of the cochlear component of CN VIII. The latency or other characteristics observed from the physiological response to the external and/or internal evoking signals sent to CN VIII may be used to determine various neuro-transmission characteristics of a particular patient.

The implantable medical system 250 and/or the external stimulation system 210 may also target cranial nerve IX (CN IX), which is the glossopharyngeal nerve. The glossopharyngeal nerve includes various components, such as the bronchial motor component, the visceral motor component, and the visceral sensory component. The glossopharyngeal nerve is characterized by a special sensory component and a general sensory component. The cell body locations of the CN IX are the medulla, the otic ganglion, the superior ganglion, and the inferior ganglion. The cranial exit of the CN IX is via the jugular foramen. Various sensory conditions may result from the delivery of the external and/or internal evoking signal to the CN IX. The physiological response may include a sensation when swallowing, a sensation in the sinus, or a sensation in the middle ear including balancing conditions, an effect on the tongue, and a sensation from the external ear.

The implantable medical system 250 and/or the external stimulation system 210 may also target cranial nerve X (CN X), which relates to the vagus nerve. The vagus nerve also contains many components, such as the bronchial motor components, the visceral motor components, and/or the visceral sensory component. The vagus nerve includes special sensory components and the general sensory components. The vagus nerve in the cranium contains cell bodies in the medulla neurons, proximate to the viscera, the superior ganglion, and the inferior ganglion. The cranial exit of the vagus nerve is via the jugular foramen. Various effects due to the delivery of external and/or internal evoking signal to the vagus nerve may be detected. These effects include, but are not limited to, various sensations of the muscles of the pharynx, larynx muscles of the palate, various portions of the esophagus, various sympathetic innervations of the muscles of the trachea, the bronchi, the digestive tract, and the cardiac muscles of the heart. The physiological response may include a visceral sensation from the base of the tongue, pharynx, larynx, trachea, bronchi, heart, esophagus, stomach, and/or intestine. Other sensations, such as taste from the epiglottis and palate, sensation from the external acoustic meatus, the auricle, and/ or the posterior cranial fossa may also be detectable. The physiological responses described above may be detected to determine the neuro-transmission condition of the patient based upon the external stimulation of the vagus nerve.

In another embodiment, the implantable medical system 250 and/or the external stimulation system 210 may also provide evoking signals to cranial nerve XI (CN XI), which relates to the spinal accessory nerve. The component of the spinal accessory nerve is a somatic motor component. The cell bodies of the spinal accessory nerve are located in the spinal cord. The cranial exit of the spinal accessory is the jugular foramen. The physiological responses due to evoking the spinal accessory may include motor effects to the sternocleidomastoid and the trapezium. These motor effects may be analyzed to determine the neuro-transmission condition of the patient based upon the external and/or internal evoking of the spinal accessory nerve.

In yet another embodiment, the implantable medical system 250 and/or the external stimulation system 210 may stimulate cranial nerve XII (CN XII), which relates to the hypoglossal nerve. The component of the hypoglossal nerve is a somatic motor component. The cell bodies of the hypoglossal nerve are located in the medulla. The cranial exit of the hypoglossal nerve is the hypoglossal canal. The physiological responses of external and/or internal evoking of the hypoglossal nerve may be the motor manipulation of the intrinsic and extrinsic muscles of the tongue. Therefore, an external and/or internal evoking of the hypoglossal nerve may be followed by a motor response of the tongue, the timing of which may be determined. Based upon this timing, latency and/or other neuro-transmission characteristics of the patient may be determined.

Further, external and/or internal evoking signals may be delivered to a portion of the cervical nerves, such as the greater occipital nerve and/or the lesser occipital nerve. Various physiological responses may result from the internal and/ or external evoking signal. These physiological responses may be analyzed to determine a latency and/or other neuro-transmission characteristics of a particular patient.

Figure 6A:
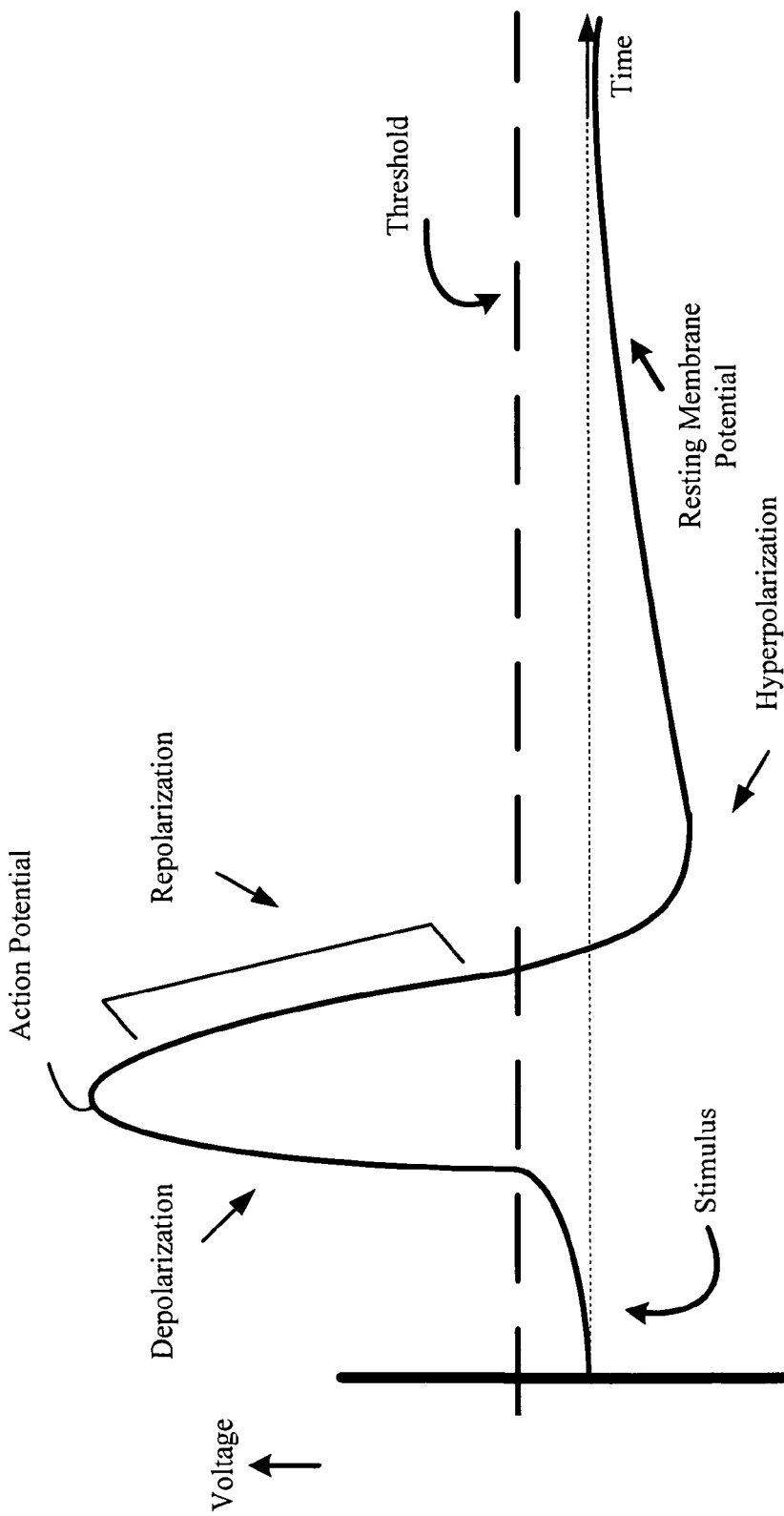
FIG. 6A illustrates an exemplary electrical signal of a firing neuron as a graph of voltage at a given location at particular times during firing by the neurostimulator of FIG. 2, when applying an electrical signal to the autonomic nerves, in accordance with one illustrative embodiment of the present invention.

FIG. 6A provides a stylized depiction of an exemplary electrical signal of a firing neuron as a graph of voltage at a given location at particular times during firing, in accordance with one embodiment of the present invention. A typical neuron has a resting membrane potential of about −70 mV, maintained by transmembrane ion channel proteins. When a portion of the neuron reaches a firing threshold of about −55 mV, the ion channel proteins in the locality allow the rapid ingress of extracellular sodium ions, which depolarizes the membrane to about +30 mV. The wave of depolarization then propagates along the neuron. After depolarization at a given location, potassium ion channels open to allow intracellular potassium ions to exit the cell, lowering the membrane potential to about −80 mV (hyperpolarization). About 1 msec is required for transmembrane proteins to return sodium and potassium ions to their starting intra- and extracellular concentrations and allow a subsequent action potential to occur. The present invention may raise or lower the resting membrane potential, thus making the reaching of the firing threshold more or less likely and subsequently increasing or decreasing the rate of fire of any particular neuron.

Figure 6B:
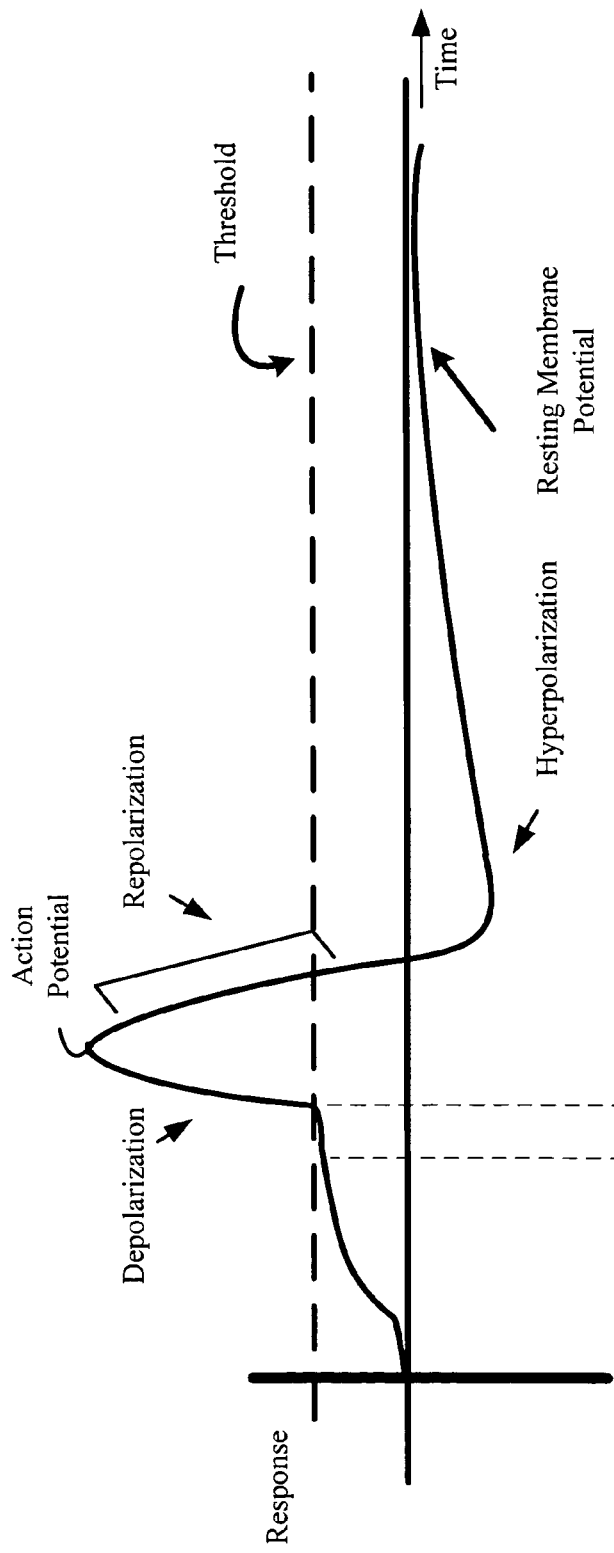
FIG. 6B illustrates an exemplary electrical signal response of a firing neuron as a graph of voltage at a given location at particular times during firing by the neurostimulator of FIG. 2, when applying a sub-threshold depolarizing-pulse and additional stimulus to the vagus nerve, in accordance with one illustrative embodiment of the present invention.
Figure 6C:
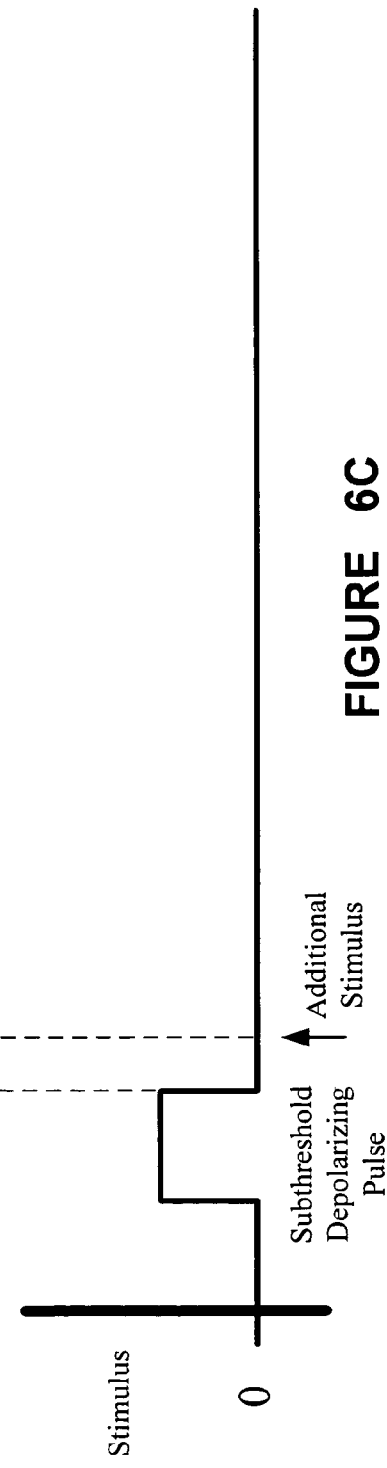
FIG. 6C illustrates an exemplary stimulus including a sub-threshold depolarizing pulse and additional stimulus to the vagus nerve for firing a neuron as a graph of voltage at a given location at particular times by the neurostimulator of FIG. 2, in accordance with one illustrative embodiment of the present invention.

Referring to FIG. 6B, an exemplary electrical signal response is illustrated of a firing neuron as a graph of voltage at a given location at particular times during firing by the neurostimulator of FIG. 2, in accordance with one illustrative embodiment of the present invention. As shown in FIG. 6C, an exemplary stimulus including a sub-threshold depolarizing pulse and additional stimulus to a cranial nerve, such as the vagus nerve 235 may be applied for firing a neuron, in accordance with one illustrative embodiment of the present invention. The stimulus illustrated in FIG. 6C depicts a graph of either current or voltage at a given location at particular times by the IMD 200.

The neurostimulator may apply the stimulus voltage of FIG. 6C to the autonomic nerve 105, which may include afferent fibers, efferent fibers, or both. This stimulus voltage may cause the response voltage shown in FIG. 6B. Afferent fibers transmit information to the brain from the extremities; efferent fibers transmit information from the brain to the extremities. The vagus nerve may include both afferent and efferent fibers, and the IMD 200 may be used to stimulate either or both.

Autonomic nerve(s) that may be stimulated by the IMD 200 may include fibers that transmit information in the sympathetic nervous system, the parasympathetic nervous system, or both. Inducing an action potential in the sympathetic nervous system may yield a result similar to that produced by blocking an action potential in the parasympathetic nervous system and vice versa.

Figure 7C:
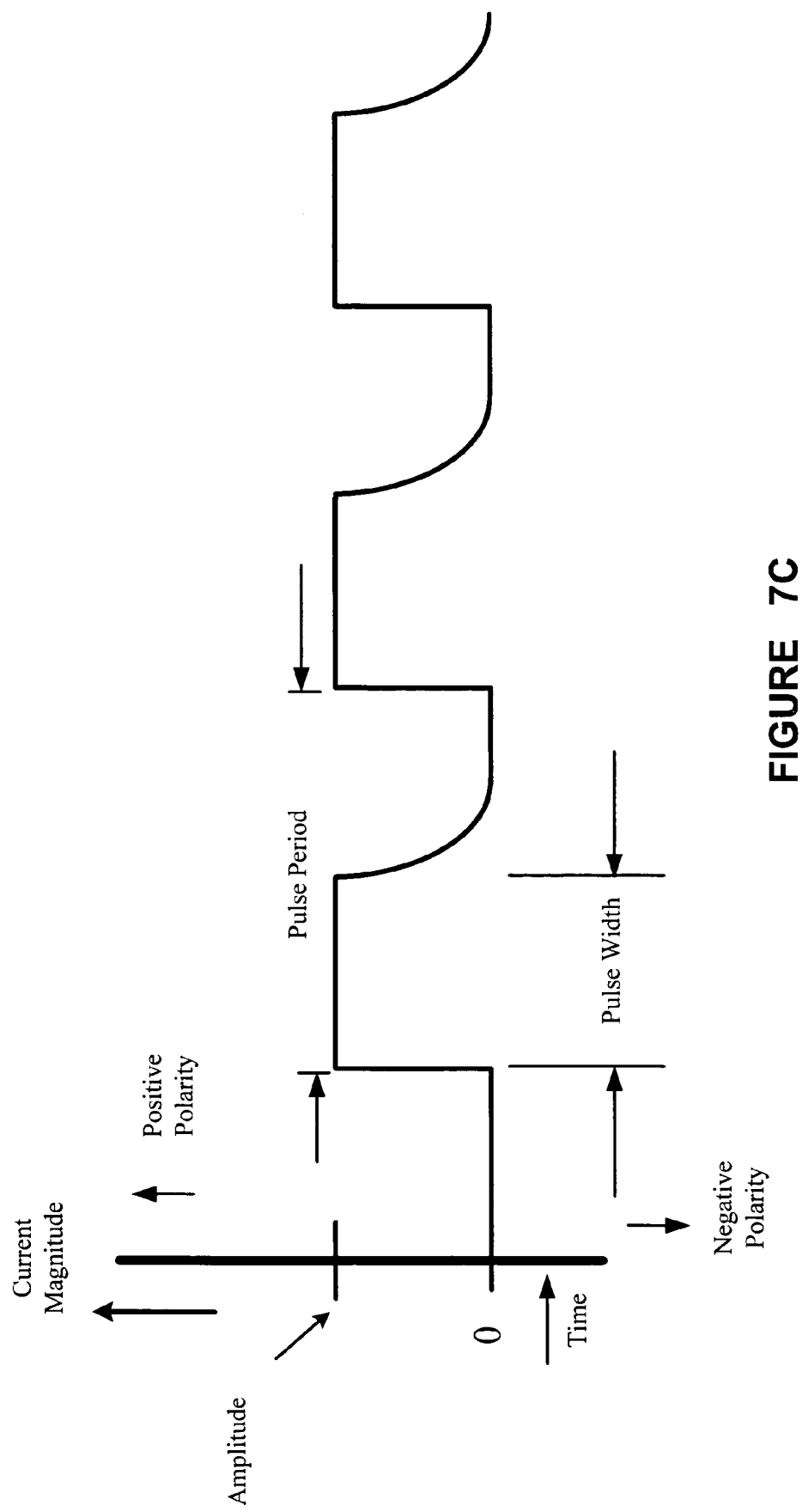

The IMD 200 may generate an electrical signal (therapeutic and/or evoking signal) according to one or more programmed parameters for therapeutic stimulation and/or evoking of an autonomic nerve, e.g., the vagus nerve. In one embodiment, the stimulation parameter may be selected from the group consisting of a current or voltage magnitude, a pulse frequency, a signal width, on-time, and off-time. An exemplary table of ranges for each of these stimulation parameters is provided in Table 1. The stimulation parameter may be of any suitable waveform; exemplary waveforms in accordance with one embodiment of the present invention are shown in FIGS. 7A-7C. Specifically, the exemplary waveforms illustrated in FIGS. 7A-7C depict the generation of the electrical signal that may be defined by a factor related to a condition relating to a mood disorder, an epilepsy disorder, an eating disorder, a hormonal disorder, a reproductive disorder, a metabolic disorder, a chronic pain disorder, and/or a heart rhythm disorder, relative to a value within a defined range.

According to one illustrative embodiment of the present invention, various electrical signal patterns may be employed by the IMD 200. These electrical signals may include a plurality of types of pulses, e.g., pulses with varying amplitudes, polarity, frequency, etc. For example, the exemplary waveform 7A depicts that the electrical signal may be defined by fixed amplitude, constant polarity, pulse width, and pulse period. The exemplary waveform 7B depicts that the electrical signal may be defined by a variable amplitude, constant polarity, pulse width, and pulse period. The exemplary waveform 7C depicts that the electrical signal may be defined by a fixed amplitude pulse with a relatively slowly discharging current magnitude, constant polarity, pulse width, and pulse period. Other types of signals may also be used, such as sinusoidal waveforms, etc. The electrical signal may be controlled current or voltage signals.

TABLE 1

| PARAMETER | RANGE |
|---|---|
| Output current | 0.1-6.0 mA |
| Pulse width | 10-1500 μsec |
| Frequency | 0.5-2500 Hz |
| On-time | 1 sec and greater |
| Off-time | 0 sec and greater |
| Frequency Sweep | 10-100 Hz |
| Random Frequency | 10-100 Hz |

On-time and off-time parameters may be used to define an intermittent pattern in which a repeating series of signals may be generated for stimulating the nerve 105 during the on-time. Such a sequence may be referred to as a "pulse burst." This sequence may be followed by a period in which no signals are generated. During this period, the nerve is allowed to recover from the stimulation during the pulse burst. The on/off duty cycle of these alternating periods of stimulation and idle periods may have a ratio in which the off-time may be set to zero, providing continuous stimulation. Alternatively, the idle time may be as long as one day or more, in which case the stimulation is provided once per day or at even longer intervals. Typically, however, the ratio of "off-time" to "on-time" may range from about 0.5 to about 10.

In one embodiment, the width of each signal may be set to a value not greater than about 1 msec, such as about 250-500 μsec, and the signal repetition frequency may be programmed to be in a range of about 20-250 Hz. In one embodiment, a frequency of 150 Hz may be used. A non-uniform frequency may also be used. Frequency may be altered during a pulse burst by either a frequency sweep from a low frequency to a high frequency, or vice versa. Alternatively, the timing between adjacent individual signals within a burst may be randomly changed such that two adjacent signals may be generated at any frequency within a range of frequencies.

Figure 8:
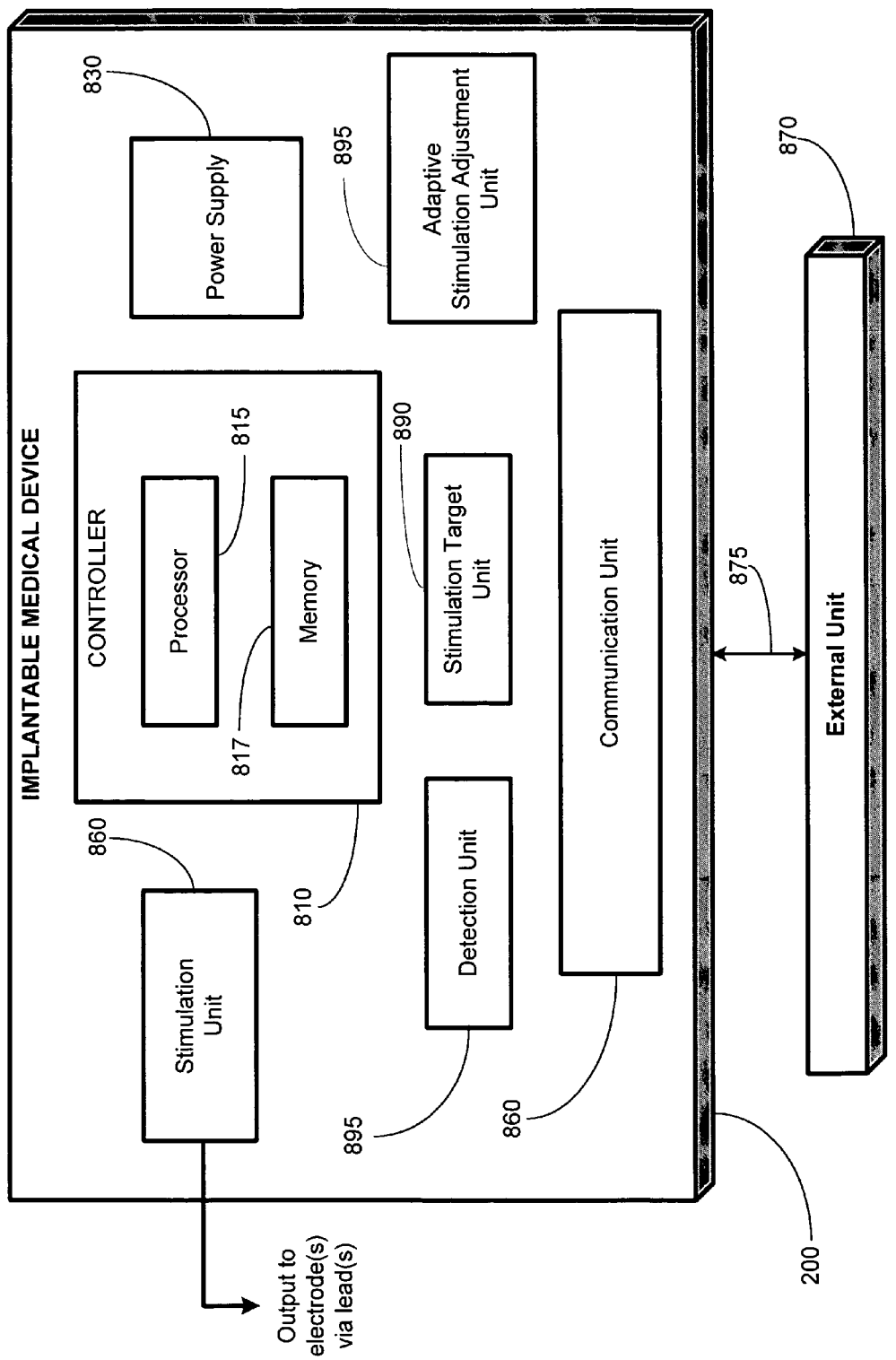
FIG. 8 provides a block diagram depiction of an implantable medical device, in accordance with one illustrative embodiment of the present invention.

Turning now to FIG. 8, a block diagram depiction of one embodiment of the IMD 200, in accordance with one illustrative embodiment of the present invention, is provided. The IMD 200 may comprise a controller 810 capable of controlling various aspects of the operation of the IMD 200. The controller 810 is capable of receiving internal data and/or external data and generating and delivering a stimulation signal to target tissues of the patient's body. For example, the controller 810 may receive manual instructions from an operator externally, or may perform stimulation based on internal calculations and programming. The controller 810 is capable of affecting substantially all functions of the IMD 200.

The controller 810 may comprise various components, such as a processor 815, a memory 817, etc. The processor 815 may comprise one or more microcontrollers, microprocessors, etc., that are capable of performing various executions of software components. The memory 817 may comprise various memory portions where a number of types of data (e.g., internal data, external data instructions, software codes, status data, diagnostic data, etc.) may be stored. The memory 817 may comprise random access memory (RAM) dynamic random access memory (DRAM), electrically erasable programmable read-only memory (EEPROM), flash memory, etc.

The IMD 200 may also comprise a stimulation unit 820. The stimulation unit 820 is capable of generating and delivering therapeutic signals and/or evoking signals to one or more electrodes via leads. A number of leads 122, 134, 137 may be coupled to the IMD 200. Therapy may be delivered to the leads 122 by the stimulation unit 820 based upon instructions from the controller 810. The stimulation unit 820 may comprise various circuitry, such as stimulation signal generators, impedance control circuitry to control the system impedance, and other circuitry that receives instructions relating to the type of stimulation to be performed. The stimulation unit 820 is capable of delivering a controlled current or voltage stimulation signal over the leads 122.

The IMD 200 may also comprise a power supply 830. The power supply 830 may comprise a battery, voltage regulators, capacitors, etc., to provide power for the operation of the IMD 200, including delivering the stimulation signal. The power supply 830 comprises a power-source battery that in some embodiments may be rechargeable. In other embodiments, a non-rechargeable battery may be used. The power supply 830 provides power for the operation of the IMD 200, including electronic operations and the stimulation function. The power supply 830 may comprise a lithium/thionyl chloride cell or a lithium/carbon monofluoride cell. Other battery types known in the art of implantable medical devices may also be used.

The IMD 200 also comprises a communication unit 860 capable of facilitating communications between the IMD 200 and various devices. In particular, the communication unit 860 is capable of providing transmission and reception of electronic signals to and from an external unit 870. The external unit 870 may be a device that is capable of programming various modules and stimulation parameters of the IMD 200. In one embodiment, the external unit 870 is a computer system that is capable of executing a data-acquisition program. The external unit 870 may be controlled by a healthcare provider, such as a physician, at a base station in, for example, a doctor's office. The external unit 870 may be a computer, preferably a handheld computer or PDA, but may alternatively comprise any other device that is capable of electronic communications and programming. The external unit 870 may download various parameters and program software into the IMD 200 for programming the operation of the implantable device. The external unit 870 may also receive and upload various status conditions and other data from the IMD 200. The communication unit 860 may be hardware, software, firmware, and/or any combination thereof. Communications between the external unit 870 and the communication unit 860 may occur via a wireless or other type of communication, illustrated generally by line 875 in FIG. 8.

The IMD 200 also comprises a detection unit 895 that is capable of detecting various conditions and characteristics physiological responses (e.g., evoked potential) due to an external and/or internal therapeutic and/or evoking signal. Various responses, such as heart rate, blood pressure, appetite, satiety, body temperature, respiration, homeostasis, brain waves (e.g., electroencephalogram), and/or evoked potentials resulting from the body stimulus (e.g., an external and/or internal therapeutic and/or evoking signal). The detection unit 895 may comprise means for deciphering data from various sensors that are capable of measuring the physiological factors described herein. Based upon the data deciphered by the detection unit 895, the IMD 200 may adjust one or more parameters relating to a therapeutic stimulus delivered by the IMD 200.

The IMD 200 may also comprise a stimulation target unit 890 that is capable of directing an internal therapeutic and/or evoking signal to one or more electrodes that is operationally coupled to various portions of the autonomic nerves. The stimulation target unit 890 may direct an internal therapeutic and/or evoking signal to various portions of a patient's body such as different portions of an autonomous nerve including, but not limited to, the left vagus main trunk, and/or the right vagus main trunk. Therefore, based upon a particular type of data detected by the detection unit 895, the stimulation target unit 890 may provide an internal therapeutic and/or evoking signal to a selective portion of an autonomic nerve to treat a disorder (e.g., a mood disorder, an epilepsy disorder, an eating disorder, a hormonal disorder, a reproductive disorder, a metabolic disorder, a chronic pain disorder, a heart rhythm disorder, and/or various other disorders. The IMD 200 may select various portions of the autonomous nerve described herein to perform an efferent, afferent, or an afferent-efferent combination stimulation in order to treat or alleviate the disorder.

The IMD 200 also comprises an adaptive stimulation adjustment unit 895. The adaptive stimulation adjustment unit 895 is capable of performing an adaptive modification of various stimulation parameters relating to an internal therapeutic and/or evoking signal. The parameters may be modified based upon assessment of a patient's neuro-transmission characteristics. Therefore, based upon the results from the internal and/or external therapeutic and/or evoking signal described above, various assessments relating to the patient's physiological characteristics (e.g., neuro-transmission characteristics) may be used by the adaptive stimulation adjustment unit 895 to perform adjustments to internal stimulation parameters. The adaptive stimulation adjustment unit 895 may perform an initial adjustment of parameters, a constant adjustment of parameters, and/or a periodic adjustment of parameters determined by a predetermined interval.

The adaptive stimulation adjustment unit 895 may receive data results from previous stimulation processes from the external unit 870. Based upon this data, the adaptive stimulation adjustment unit 895 may look up various tables that may be stored in the memory 817 to adjust various stimulation parameters. Further, the adaptive stimulation adjustment unit 895 is capable of sensing physiological data from the detection unit 895 and automatically adjusting various characteristics of the internal therapeutic and/or evoking signals described above. The adaptive stimulation adjustment unit 895 may be a software, hardware or a firmware unit that is a stand-alone module, or alternatively, a module that is integrated into the controller 810.

The adaptive stimulation adjustment unit 895 may detect any adverse results based on a particular therapeutic stimulation and deem it to be an adverse therapeutic stimulation. The adverse therapeutic stimulation may then be modified such that subsequent therapeutic stimulation regimes do not provide undesirable results. This may be performed, for example, by detecting adverse physiological responses after the delivery of an internal and/or an external stimulation signal. The adaptive stimulation adjustment unit 895 may then correlate various adverse physiological results to one or more stimulation parameters. Upon performing calculations, the adaptive stimulation adjustment unit 895 may modify one or more therapeutic stimulation parameters and continually check the physiological results until a determination is made that no substantially adverse physiological responses above a tolerable level are detected based upon the delivered stimulation. The physiological conditions that are checked may include various conditions, such as heart rate, blood pressure, respiration, homeostasis, brain waves, and/or evoked potentials resulting from a evoking signal.

One or more blocks illustrated in the block diagram of IMD 200 in FIG. 8 may comprise hardware units, software units, firmware units and/or any combination thereof. Additionally, one or more blocks illustrated in FIG. 8 may be combined with other blocks, which may represent circuit hardware units, software algorithms, etc. Additionally, any number of the circuitry or software units associated with the various blocks illustrated in FIG. 8 may be combined into a programmable device, such as a field programmable gate array, an ASIC device, etc.

Figure 9:
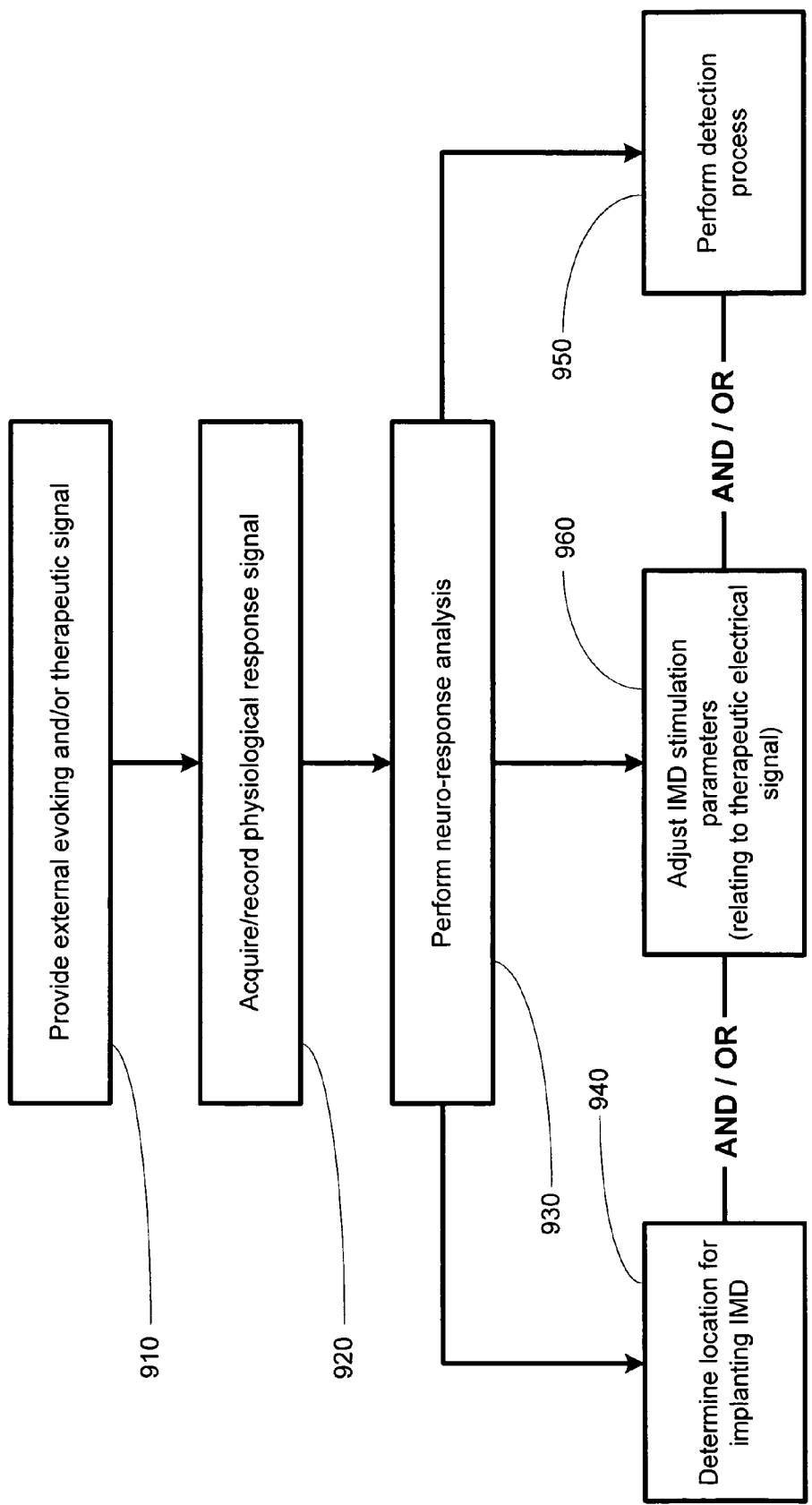
FIG. 9 provides a flowchart depiction of a method for adjusting the IMD stimulation parameters using an external evoking signal, in accordance with one illustrative embodiment of the present invention.

Embodiments of the present invention provide for applying a sensory and/or a motor evoking signal to a patient's body and monitoring a physiological response to the stimulus. A characteristic of the physiological response (e.g., a neurotransmission characteristic of a particular portion of the patient's body, such as the vagus nerve) may be determined. Based upon the characteristic(s) of the physiological response, a stimulation parameter relating to a neurostimulation provided by the IMD 200 may be determined. The sensory or motor stimulus may be provided by an external signal source, an internal signal source (e.g., the IMD 200), and/or a combination of the external and internal signal sources. FIG. 9 illustrates a flowchart depiction of the steps of the method relating to providing a sensory and/or motor stimulation using an external stimulation source, in accordance with one illustrative embodiment of the present invention.

An external evoking and/or therapeutic signal may be provided to a patient (block 910). The external stimulation system 210 is capable of providing an evoked potential in a portion of the patient's body. The evoked potential may include an alteration of the normally or randomly occurring electrical activity in the patient's body. The electrical activity relating to the evoked potential may be a result of a stimulus that is exogenously applied (i.e., from a source other than the patient's own body) electrical, chemical, auditory, visual, and/or mechanical signals applied to the neural structure. External evoking and/or therapeutic signals may be provided by various external stimulation techniques, such as a transcranial magnetic stimulation system, an electrical stimulation system that may use a transcranial technology and/or electrodes to target specific areas of the patient's body, an auditory stimulation, and/or any stimulus that may evoke a change in the normal or randomly occurring electrical activity in the patient's body.

Based upon the external evoking and/or therapeutic signal, the resultant physiological responses in response to the external stimulation, is acquired and/or recorded (block 920). The acquisition of the resultant effects may be acquired by various types of sensors that are capable of acquiring various physiological characteristics of the patient. In one embodiment, a physiological characteristic comprises at least one neuro-transmission characteristic. Using the resultant data relating to the physiological responses, a neuro-response analysis may be performed (block 930). The neuro-response analysis may entail various techniques to analyze and correlate external evoking and/or therapeutic signal(s) with various physiological conditions. Studies such as latency analysis may be performed. The latency analysis may relate to the time period between the time of providing stimulation, and the onset of a predetermined amount of physiological response(s). Other neuro-transmission characteristics may also be analyzed using the resultant data. A more detailed description of the neuro-response analysis of block 930 is provided in FIG. 10 and accompanying description below.

Continuing referring to FIG. 9, upon performing the neuro-response analysis of block 930, various steps may be implemented. For example, upon performing the neuro-response analysis, a determination as to where in the patient's body to implant the IMD 200 may be made (block 940). As described above, based upon the neuro-transmission characteristics of a nerve, such as the vagus nerve of the patient, the left side vagus nerve, the right side vagus nerve, or both, may be slated for therapeutic stimulation. This determination may then be used to decide whether to implant the IMD 200 on the left side or in the right side of the patient's body. A more effective stimulation regimen may be achieved by predetermining the better location for implanting the IMD and the related accessories, such as the electrodes and the leads. Further, based upon the patient's response to an external or internal evoking and/or therapeutic signal, an analysis may be performed to determine whether therapeutic stimulation may be sufficiently effective for that patient.

Upon performing the neuro-response analysis, a selection of a target location for delivering therapeutic stimulation may also be performed (block 950). This process may include identifying an optimum location for delivering therapeutic stimulation based upon the neuro-response analysis. Depending on the disorder being treated and the projected efficacy of a particular location of the patient's body (i.e., the particular location on the vagus nerve), a target may be established for delivery of therapeutic stimulation. In this manner, more effective therapeutic stimulation may be provided by the IMD 200.

Further, upon performing the neuro-response analysis of block 930, an adjustment of the therapeutic stimulation parameters used by the IMD 200 may be performed (block 960). Such adjustment(s) may involve adjusting various characteristics of the signal relating to the therapeutic stimulation based upon specific physiological characteristics of the patient. For example, based upon the latency related to the neuro-response of a particular patient, a signal with higher amplitude or greater frequency characteristics may be employed for therapeutic stimulation, which may overcome any excessive latency attributed to a particular person. Various other stimulation parameter adjustments may be performed depending on the characteristics of the neuro-response of a particular patient.

Figure 10:
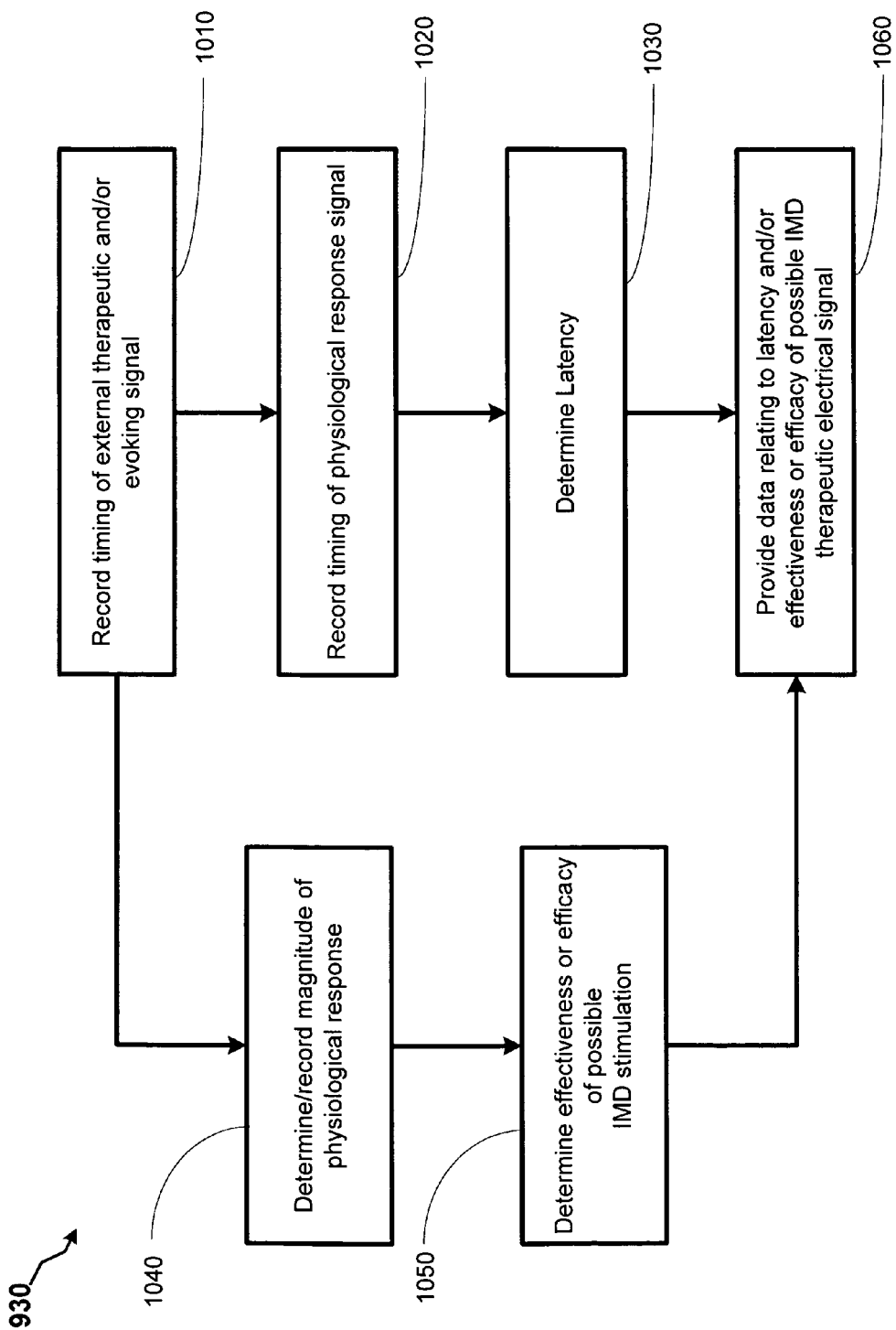
FIG. 10 provides a more detailed flowchart depiction for the steps for performing a neuro-response analysis of FIG. 9, in accordance with one illustrative embodiment of the present invention.

Turning now to FIG. 10, a more detailed flowchart depiction of the steps for performing the neuro-response analysis of block 930 of FIG. 9, is provided. Upon delivering the external evoking and/or therapeutic signal(s), the timing of the signal delivery may be recorded (block 1010). Further, the timing of the resulting physiological response in response to the external stimulation may also be recorded (block 1020). The respective timing of the delivery of the external evoking and/or therapeutic signal and the detection of the resultant physiological response(s) may be used to determine the latency of the neuro-transmission of a portion of the patient's body (block 1030).

Additionally, a determination may be made as to the magnitude and/or other characteristics of the resulting physiological response in response to the external evoking and/or therapeutic signal (block 1040). The physiological response may be related to the neuro-transmission characteristics of various portions of the patient's body. The analysis to determine the characteristics of the physiological response may include determining whether a parameter related to the physiological response exceeds said a value related to a threshold value, a subthreshold value, a reference value, a comparison value, a calculated value, a value derived from diagnosis, a predetermined value, and/or a baseline value, among other factors. Therefore, the latency, as well as the magnitude and/or other characteristics of the response due to a delivered evoking and/or therapeutic signal may be recorded and analyzed. This may provide an indication as to various characteristics of the physiology of the patient's body. This information may be used to determine the effectiveness or efficacy of a potential therapeutic stimulation that may be delivered by the IMD 200 (block 1050). Based upon the data relating to the effectiveness of the evoking and/or therapeutic signal, as projected, as well as the latency data indicated by the neuro-transmission characteristics of the patient, an analysis may be performed to provide data relating to the physiological characteristics of the patient's body (block 1060). This may include data relating to the latency and/or effectiveness or efficacy of a possible therapeutic electrical signal. Therefore, even before delivery of a therapeutic stimulation, various feedback optimizations of the therapeutic stimulation parameters may be defined by using data resulting from the external stimulation and/or any internal stimulation.

Figure 11:
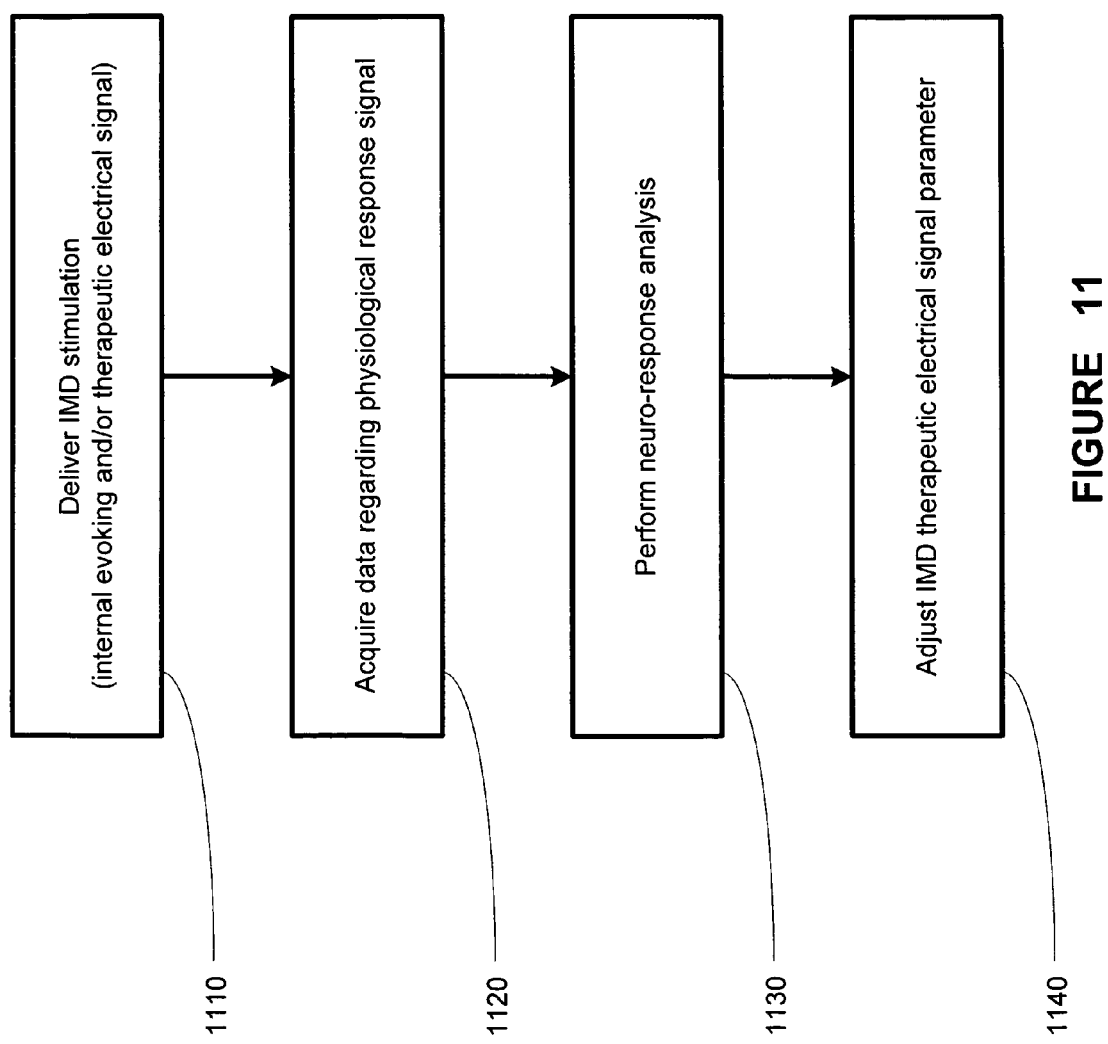
FIG. 11 provides a flowchart depiction of performing an adaptive adjustment of stimulation parameters, in accordance with one illustrative embodiment of the present invention.

Turning now to FIG. 11, a flowchart depiction of delivering an internal stimulation to adjust therapeutic stimulation parameters, in accordance with one illustrative embodiment of the present invention is provided. The IMD 200 may deliver an internal evoking and/or therapeutic signal to a portion of a patient's body (block 1110). In an alternative embodiment, an external evoking and/or therapeutic signal may also be provided to the patient's body. The delivery of the internal and/or external evoking and/or therapeutic signal may be coordinated as to the timing, location, intensity, and/or other characteristics of the evoking and/or therapeutic signals. Based upon the evoking and/or therapeutic signal, the IMD 200 or an external sensing system, may detect and acquire various physiological responses that may result from the evoking and/or therapeutic signal provided (block 1120). The physiological response may include various characteristics, such as heart rate, blood pressure, appetite, satiety, body temperature, respiration, homeostasis, brain waves, evoked potentials, and other responses. Input from the patient may also be provided as a response, such as mood characteristics, etc.

Based upon the physiological response, a neuro-response analysis may be performed by the IMD 200 (block 1130). The neuro-response analysis for the internal evoking and/or therapeutic signal may be similar to the analysis for the external evoking and/or therapeutic signal described in FIG. 10. Further, the neuro-response analysis may include detecting whether any adverse physiological responses have been detected, and if so, a particular evoking and/or therapeutic signal may be deemed as an adverse signal. Based upon the neuro-response analysis, an adjustment to the therapeutic electrical signal parameter may then be performed (block 1140). This adjustment may include changing the value of various parameters used to determine the characteristic of a particular therapeutic stimulation signal. The parameters may include, but are not limited to, a pulse width, a polarity, a pulse frequency, a current or voltage amplitude, an on-time, and an off-time, and a phase characteristic of a therapeutic stimulation signal.

This process may be continuously repeated until no adverse stimulation signal is found. Alternatively, this process may be performed periodically or continuously, or in an adaptive manner. The adaptive process may relate to detecting various physiological responses due to an internal and/or external stimulation in predetermined intervals or in a continuous fashion. Based upon the determination that adverse effects have been found, an adaptive correction or adjustment to various therapeutic stimulation parameters may be made to improve the quality and the effectiveness of the therapeutic stimulation.

Therefore, using embodiments of the present invention, results from an external and/or an internal evoking and/or therapeutic signal may be used to optimize or improve therapeutic stimulation provided by an external and/or internal medical device Further, the external and/or internal medical device may also perform an adaptive adjustment of therapeutic stimulation parameters based on various observation of the physiological responses described above. Utilizing embodiments of the present invention, a more effective therapeutic stimulation may be provided by an external and/or internal medical device.

All of the methods and apparatus disclosed and claimed herein may be made and executed without undue experimentation in light of the present disclosure. While the methods and apparatus of this invention have been described in terms of particular embodiments, it will be apparent to those skilled in the art that variations may be applied to the methods and apparatus and in the steps or in the sequence of steps of the method described herein without departing from the concept, spirit, and scope of the invention, as defined by the appended claims. It should be especially apparent that the principles of the invention may be applied to selected cranial nerves other than the vagus nerve to achieve particular results.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed:

1. A method for affecting a neuromodulation therapy based upon an external evoking signal applied to a patient's body, comprising:
    applying an external evoking signal to a first target portion of a patient's body;
    receiving data relating to a physiological response resulting from applying said external evoking signal to the patient's body;
    determining a neurotransmission characteristic of said patient's body based upon said data relating to the physiological response; and
    controlling at least one parameter defining a therapeutic electrical stimulation signal provided by an implantable medical device based upon said neurotransmission characteristic to treat a disorder.

2. The method of claim 1, wherein receiving said data relating to a physiological response resulting from applying said external evoking signal comprises sensing a physiological response to said external evoking signal.

3. The method of claim 2, wherein applying an external evoking signal to a first target portion of a patient's body comprises providing at least one of a transcranial magnetic stimulation, a transcranial electrical stimulation, and a delivery of an electrical signal to a neural structure.

4. The method of claim 1, wherein applying an external evoking signal to a first target portion of a patient's body comprises delivering said external evoking signal to at least one of:
    a cervical nerve selected from a group consisting of a greater occipital nerve and a lesser occipital nerve, and
    a cranial nerve.

5. The method of claim 1, wherein said neurotransmission characteristic is selected from the group consisting of a time delay between delivery of the external evoking signal and the physiological response, the magnitude of a physiological response signal, a frequency of a physiological response signal, a conduction velocity of a physiological response signal, a physiological response signal latency, a spectral analysis characteristic of a physiological response signal, an onset latency, an interpeak latency, a signal morphology, a signal polarity, and a signal dispersion.

6. The method of claim 1, wherein controlling at least one parameter defining said therapeutic electrical stimulation signal provided by an implantable medical device comprises controlling a parameter selected from a group consisting of a pulse width, a polarity, a pulse frequency, a current or voltage amplitude an on-time, an off-time, and a phase characteristic, wherein said parameter is selected to treat the disorder.

7. A method for affecting a neuromodulation therapy based upon an external evoking signal applied to a patient's body, comprising:
    applying an external evoking signal to a first target portion of a patient's body;
    receiving data relating to a physiological response resulting from applying said external evoking signal to the patient's body;
    determining a neurotransmission characteristic of said patient's body based upon said data relating to the physiological response; and
    determining at least one of a cranial nerve location and a cervical nerve location at which to couple an electrode for delivering a therapeutic electrical stimulation signal based on said neurotransmission characteristic.

8. A method for identification of a patient as a candidate for a neurostimulation therapy based upon an external evoking signal applied to the patient's body, comprising:
    applying an external evoking signal to a first target portion of a patient's body;
    receiving data relating to a physiological response resulting from applying said external evoking signal to the patient's body;
    determining a neurotransmission characteristic of said patient's body based upon said data relating to the physiological response; and
    determining whether said patient is a potential candidate for a neurostimulation therapy based on said neurotransmission characteristic.

9. A method for controlling a therapeutic stimulation signal provided by an implantable medical device based upon an external signal applied to the patient's body, comprising:
    applying a first signal to a portion of a patient's body from a source external to said implantable medical device;
    receiving data relating to a physiological response resulting from said first signal;

determining a neurotransmission characteristic of said patient's body based upon said data relating to said physiological response; and adjusting at least one parameter defining a therapeutic stimulation signal provided by said implantable medical device based upon said neurotransmission characteristic to treat a disorder.

10. The method of claim 9, wherein providing said first stimulation signal to said portion of the patient's body comprises providing at least one of a transcranial magnetic stimulation, a transcranial electrical stimulation, and a delivery of a neurostimulation signal selected from the group consisting of a deep brain stimulation, a cranial nerve stimulation, and a spinal cord stimulation.

11. The method of claim 9, wherein determining said neurotransmission characteristic of said patient's body comprises determining a characteristic selected from the group consisting of a time delay between delivery of a said first signal and a physiological response, the magnitude of a physiological response signal, a frequency of a physiological response signal, a conduction velocity of a physiological response signal, a physiological response signal latency, a spectral analysis characteristic of a physiological response signal, an onset latency, an interpeak latency, a signal morphology, a signal polarity, and a signal dispersion.

12. A medical device system for providing a neurostimulation therapy, comprising:

at least one external stimulation system for delivering a first external evoking signal to a first portion of a patient's body; and at least one implantable medical device (IMD) for delivering a therapeutic electrical signal to a second portion of said patient's body, wherein said IMD comprises a controller to receive data relating to a physiological response resulting from said first external evoking signal, the controller to also determine a neurotransmission characteristic of said patient's body based upon said data relating to the physiological response, and to control at least one parameter defining said therapeutic electrical signal based upon said neurotransmission characteristic to treat a disorder.

13. The medical device system of claim 12, further comprising:

at least one electrode operatively coupled to said IMD and to said second portion of the patient's body, said electrode to deliver said therapeutic electrical signal; and at least one device communicatively coupled to said IMD and to said external stimulation system, said device to receive said data relating to a physiological response resulting from said external stimulation system and provide said data to said IMD.

14. The medical device system of claim 12, wherein said external stimulation system comprises:

a transcranial stimulation system for delivering at least one of an electrical evoking signal and a magnetic evoking signal to said first portion of said patient's body; and a sensor for detecting said physiological response.

15. The medical device system of claim 12, wherein said first portion of said patient's body is a portion selected from a group consisting of the head, the face, and the neck of the patient.

* * * * *